US008735803B2

(12) United States Patent
Ford et al.

(10) Patent No.: US 8,735,803 B2
(45) Date of Patent: May 27, 2014

(54) MULTI-CHANNEL DETECTOR ASSEMBLY FOR DOWNHOLE SPECTROSCOPY

(75) Inventors: Jess V. Ford, Weatherford, TX (US); Thomas Blankinship, Fort Worth, TX (US); Bryan W. Kasperski, Crowley, TX (US); Margaret C. Waid, Aledo, TX (US); Sean M. Christian, Land O Lakes, FL (US)

(73) Assignee: Precision Energy Services, Inc, Fort Worth, TX (US)

( * ) Notice: Subject to any disclaimer, the term of this patent is extended or adjusted under 35 U.S.C. 154(b) by 924 days.

(21) Appl. No.: 12/613,808

(22) Filed: Nov. 6, 2009

(65) Prior Publication Data

US 2011/0108720 A1 May 12, 2011

(51) Int. Cl.
*G01V 5/04* (2006.01)

(52) U.S. Cl.
USPC ............................................. 250/262

(58) Field of Classification Search
USPC ............................................. 250/262
See application file for complete search history.

(56) References Cited

U.S. PATENT DOCUMENTS

| | | | |
|---|---|---|---|
| 3,193,676 A | 7/1965 | Smart | |
| 3,941,483 A | 3/1976 | Ferrin | |
| 4,264,205 A | 4/1981 | Landa | |
| 4,285,596 A | 8/1981 | Landa | |
| 4,412,744 A | 11/1983 | Lee et al. | |
| 4,525,627 A | 6/1985 | Krempl et al. | |
| 4,692,621 A | 9/1987 | Passaro et al. | |
| 4,785,806 A | 11/1988 | Deckelbaum | |
| 4,832,490 A | 5/1989 | Boos | |
| 4,962,815 A | 10/1990 | Schultz et al. | |
| 4,968,148 A | 11/1990 | Chow | |
| 4,994,671 A | 2/1991 | Safinya et al. | |
| 5,128,797 A | 7/1992 | Sachse et al. | |
| 5,166,747 A | 11/1992 | Schroeder et al. | |
| 5,167,149 A | 12/1992 | Mullins et al. | |
| 5,170,056 A | 12/1992 | Berard | |
| 5,173,808 A | 12/1992 | Auer et al. | |

(Continued)

FOREIGN PATENT DOCUMENTS

| | | |
|---|---|---|
| GB | 2391939 A | 2/2004 |
| WO | 81/00775 | 3/1981 |

(Continued)

OTHER PUBLICATIONS

Notice of Allowance in co-pending U.S. Appl. No. 12/613,700, mailed Dec. 20, 2011.

(Continued)

*Primary Examiner* — David Porta
*Assistant Examiner* — Kenneth J Malkowski
(74) *Attorney, Agent, or Firm* — Wong, Cabello, Lutsch, Rutherford & Brucculeri LLP

(57) ABSTRACT

A multi-channel detector assembly for downhole spectroscopy has a reference detector unit optically coupled to a reference channel of a source and has a measurement detector unit optically coupled to a measurement channel of the source. The reference and measurement detectors detect spectral signals across a spectral range of wavelengths from the reference and measurement channels. Conversion circuitry converts the detected spectral signals into reference signals and measurement signals, and control circuitry processes the reference and measurements signals based on a form of encoding used by the source. Then, the control circuitry can control the output of spectral signals from the source based on the processed signals or scale the measurement signal to correct for source fluctuations or changes in environmental conditions.

40 Claims, 8 Drawing Sheets

(56) References Cited

U.S. PATENT DOCUMENTS

| | | |
|---|---|---|
| 5,257,086 A | 10/1993 | Fateley et al. |
| 5,337,621 A | 8/1994 | Spease |
| 5,371,543 A | 12/1994 | Anderson |
| 5,401,966 A | 3/1995 | Gray et al. |
| 5,440,118 A | 8/1995 | Roscoe |
| 5,475,221 A | 12/1995 | Wang |
| 5,504,575 A | 4/1996 | Stafford |
| 5,557,398 A | 9/1996 | Wechsler et al. |
| 5,629,125 A | 5/1997 | Leblans et al. |
| 5,825,478 A | 10/1998 | Wilcox |
| 5,828,066 A | 10/1998 | Messerschmidt |
| 5,859,430 A | 1/1999 | Mullins et al. |
| 5,966,484 A | 10/1999 | Yuuki |
| 6,064,488 A | 5/2000 | Brand et al. |
| 6,075,595 A | 6/2000 | Malinen |
| 6,128,078 A | 10/2000 | Fateley |
| 6,301,959 B1 | 10/2001 | Hrametz et al. |
| 6,388,251 B1 | 5/2002 | Papanyan |
| 6,420,695 B1 | 7/2002 | Grasdepot |
| 6,429,936 B1 | 8/2002 | Scaduto |
| 6,437,326 B1 | 8/2002 | Yamate et al. |
| 6,465,775 B2 | 10/2002 | Mullins et al. |
| 6,476,384 B1 | 11/2002 | Mullins et al. |
| 6,504,943 B1 | 1/2003 | Sweatt et al. |
| 6,559,945 B1 | 5/2003 | Grasdepot |
| 6,571,118 B1 | 5/2003 | Utzinger et al. |
| 6,600,591 B2 | 7/2003 | Anderson et al. |
| 6,678,050 B2 | 1/2004 | Pope et al. |
| 6,693,701 B2 | 2/2004 | Hansen |
| 6,753,960 B1 | 6/2004 | Polynkin et al. |
| 6,768,105 B2 | 7/2004 | Mullins et al. |
| 6,781,691 B2 | 8/2004 | MacKinnon et al. |
| 6,798,518 B2 | 9/2004 | DiFoggio et al. |
| 6,870,619 B1 | 3/2005 | Tenhunen et al. |
| 6,939,717 B2 | 9/2005 | Jiang |
| 6,995,360 B2 | 2/2006 | Jones et al. |
| 7,013,723 B2 | 3/2006 | Ramakrishnan et al. |
| 7,265,830 B2 | 9/2007 | Wang |
| 7,279,678 B2 | 10/2007 | Andrews et al. |
| 7,280,214 B2 | 10/2007 | DiFoggio et al. |
| 7,321,428 B2 | 1/2008 | Hunt |
| 7,336,356 B2 | 2/2008 | Vannuffelen et al. |
| 7,360,924 B2 | 4/2008 | Henson et al. |
| 7,362,422 B2 | 4/2008 | DiFoggio et al. |
| 7,379,180 B2 | 5/2008 | Vannuffelen |
| 7,403,680 B2 | 7/2008 | Simbal |
| 7,508,506 B2 | 3/2009 | Christian et al. |
| 7,609,380 B2 | 10/2009 | Vannuffelen et al. |
| 7,782,389 B2 | 8/2010 | Neidrich |
| 7,782,460 B2 | 8/2010 | DiFoggio et al. |
| 8,164,050 B2 | 4/2012 | Ford et al. |
| 8,436,296 B2 | 5/2013 | Ford et al. |
| 2003/0206026 A1 | 11/2003 | Diakonov et al. |
| 2004/0069942 A1 | 4/2004 | Fujisawa et al. |
| 2004/0149915 A1 | 8/2004 | Goncalves |
| 2004/0169858 A1 | 9/2004 | Da Silva |
| 2004/0201850 A1 | 10/2004 | Hajian et al. |
| 2004/0239923 A1 | 12/2004 | Adams et al. |
| 2004/0239931 A1 | 12/2004 | Teichmann et al. |
| 2005/0185179 A1 | 8/2005 | Wang |
| 2005/0243312 A1 | 11/2005 | Geshwind et al. |
| 2005/0275844 A1 | 12/2005 | Kaltenbacher |
| 2006/0243033 A1 | 11/2006 | Freemark et al. |
| 2007/0013911 A1 | 1/2007 | DiFoggio |
| 2007/0035737 A1 | 2/2007 | Andrews et al. |
| 2007/0109537 A1 | 5/2007 | Vannuffelen |
| 2007/0159625 A1 | 7/2007 | DiFoggio |
| 2007/0171412 A1 | 7/2007 | Vannuffelen |
| 2007/0171414 A1 | 7/2007 | Vannuffelen |
| 2007/0229821 A1 | 10/2007 | Christian et al. |
| 2008/0078544 A1 | 4/2008 | Christian |
| 2008/0087078 A1 | 4/2008 | Vannuffelen |
| 2008/0165356 A1 | 7/2008 | DiFoggio et al. |
| 2008/0173083 A1 | 7/2008 | Kasperski et al. |
| 2008/0174777 A1 | 7/2008 | Carron |
| 2009/0161358 A1 | 6/2009 | Tusutsui |

FOREIGN PATENT DOCUMENTS

| | | |
|---|---|---|
| WO | 95/04263 | 2/1995 |
| WO | 2009050081 A2 | 4/2009 |
| WO | 2009126636 | 10/2009 |

OTHER PUBLICATIONS

European Search Report for Application No. EP 10188545, dated Feb. 14, 2011.
Cantrell, "The SLIM Spectrometer" Anal. Chem. 2003, 75, pp. 27-35, Department of Chemistry, Oregon State University, 153 Gilbert Hall, Corvallis, Oregon 97331-4001.
Hauser, "A Multi-Wavelength Photometer Based on Light-Emitting Diodes" Talanta, vol. 42, No. 4, pp. 605-612, 1995.
Malinen et al., Sensors and Actuators B 51 (1998) 220-224,"LED-based NIR spectrometer module for hand-held and process analyser applications," dated Jun. 16, 1998.
O'Toole, "Absorbance Based Light Emitting Diode Optical Sensors and Sensing Devices," Sensors 2008, 8, pp. 2453-2479; dated Apr. 7, 2008 obtained from www.mdpi.org/sensors.
Palma, "Portable light-emitting diode-based photometer with one-shot optochemical sensors for measurement in the field," dated Oct. 21, 2008, American Institute of Physics.
Schlumberger, "Fundamentals of Formation Testing," © 2006, pp. 1-5, 27-29, 55-67, 99-124, 199-202, Schlumberger Marketing Communications, Sugar Land, Texas, United States.
Schlumberger, "Engineering the Next-Generation Downhole Fluid Analysis Tool," dated May 7, 2007.
OZ Optics, "Silicon Optical Bench Platforms," dated Nov. 14, 2002, obtained from www.ozoptics.com.
Yeh, "A Low Cost LED Based Spectrometer," Journal of the Chinese Chemical Society, 2006, 53, pp. 1067-1072.
Frentress, "Field Photometer with Nine-Element Filter Wheel," dated Feb. 1964, vol. 3, No. 2, Applied Optics, pp. 303-308.
International Search Report and Written Opinion received in corresponding Application No. PCT/US07/82221, dated May 5, 2008.
International Search Report, International Patent Application No. PCT/US07/080112, mailed on Mar. 25, 2008.
Wagner, Eugene P. II, et al., "Construction and Evaluation of a Visible Spectrometer Using Digital Micromirror Spatial Light Modulation," Applied Spectroscopy, vol. 49, No. 11, 1995.
Ford, Joseph E., et al., "Dynamic Spectral Power Equalization Using Micro-Opto-Mechanics," IEEE Photonics Technology Letters, vol. 10, No. 10, Oct. 1998.
Duncan, Walter M., "Dynamic Optical Filtering in DWDM Systems Using the DMD," Solid State Electronics 46 (2002), pp. 1583-1585.
Lerner, J.M., et al., "The Optics of Spectroscopy—A Tutorial," Instruments SA, Inc., 1988.
Spudich, Thomas M., et al., "Potential for using a Digital Micromirror Device as a Signal Multiplexer in Visible Spectrscopy," Applied Spectroscopy, vol. 57, No. 7, 2003.
DeVerse, R. A., et al, "Realization of the Hadamard Multiplex Advantage Using a Programmable Optical Mask in a Dispersive Flat-Field Near-Infrared Spectrometer," Applied Spectroscopy, vol. 54, No. 12, 2000.
Badry, R., et al., "Downhole Optical Analysis of Formation Fluids," Oilfield Review, Jan. 1994.
Schroeder, R., "Slick Engineering," Spie's OE Magazine, May 2003.
Raghuraman, B., "Real-Time Downhold pH Measurement Using Optical Spectroscopy," SPE 93057, Society of Petroleum Engineers, 2005.
Sirkis, J., "Multifunctionality The Key in Challenging Instrumentation Markets," Lightwave Magazine, Mar. 2003.
Meyer, R., "RITMOS: A Micromirror-Based Multi-Object Spectrometer," Proceedings of the SPIE, 2004.
Smits, A.R., "In-Situ Optical Fluid Analysis as an Aid to Wireline Formation Sampling," SPE Formation Evaluation, Jun. 1995.

(56) References Cited

OTHER PUBLICATIONS

Texas Instruments, Application Report, "Single Panel DLP Projection System Optics," Mar. 2005.
Texas Instruments, Product Preview, "DMD 0.7 XGA 12.degree. LVDS DMD Discovery," Jul. 2005.
Texas Instruments, Product Preview Data Sheet, "DMD 0.7 XGA 12.degree. DDR DMD Discovery," Aug. 30, 2005.
Texas Instruments, "DMD Discovery 1100 Chip Set," 2004.
Texas Instruments, "DMD Discovery 3000 Digital Controller (DDC3000) Starter Kit Technical Reference Manual," Oct. 2005.
Texas Instruments, "DMD Discovery 1100 Controller Board and Starter Kit," Oct. 2004.
Baker Hughes, "RCI Reservoir Characterization Instrument," obtained from www.bakerhughesdirect.com, generated on Apr. 8, 2010.
Baker Hughes, "SampleView" 2000, obtained from www.bakerhughesdirect.com, generated on Apr. 19, 2010.
First Examination Report in counterpart Canadian Appl. No. 2,718,452, dated Apr. 4, 2012.
First Examination Report in counterpart Canadian Appl. No. 2.725.359, dated Feb. 28, 2012.
First Office Action in co-pending U.S. Appl. No. 12/613,700, dated Jul. 8, 2011.
Reply to First Office Action dated Jul. 8, 2011 in co-pending U.S. Appl. No. 12/613,700, filed Nov. 28, 2011.
First Examination Report in counterpart Australian Appl. No. 2010227019, dated Jul. 22, 2011.
First Office Action in co-pending U.S. Appl. No. 12/613,665, mailed Aug. 26, 2011.
Reply to First Office Action mailed Aug. 26, 2011 in co-pending U.S. Appl. No. 12/613,665, filed Nov. 28, 2011.
First Examination Report in counterpart Australian Appl. No. 20100227020, dated Jul. 22, 2011.
Examiner's First Report in corresponding Australian Patent App. No. 2010227021, dated May 26, 2011.
First Office Action received in in related U.S. Appl. No. 13/452,128, mail date Dec. 12, 2012.
Notice of Allowance received in related U.S. Appl. No. 13/452,128, mail date May 6, 2013.
Office Action received in related U.S. Appl. No. 12/613,665, mail date Jun. 20, 2012.
Reply to Office Action dated Jun. 20, 2012 in related U.S. Appl. No. 12/613,665, filed Nov. 8, 2012.
Final Office Action received in related U.S. Appl. No. 12/613,665, mail date Dec. 6, 2011.
Reply to Final Office Action dated Dec. 6, 2011 in related U.S. Appl. No. 12/613,665, filed Jun. 6, 2012.
Choi J G et al., KR 2002060005 A, published Jul. 16, 2002.
European Search Report received in related EP Appl. No. EP 10188530, dated Jun. 27, 2013.
European Search Report received in counterpart EP Appl. No. EP 10188524, dated Jun. 28, 2013.
Keranen, "Analytic and Raytrace Modeling of a Miniaturized Infrared Spectrometer Module," obtained from http://techconnect.org/publications/MSM/2000/pdf/W42.02.pdf, PDF document indicating date created of May 6, 2000.
Thorlabs Inc., "Stepped Circular Neutral Density Filter," Drawing No. 10661-E01, Part No. NDC-100S-4, obtained from obtained from http://www.thorlabs.com/, PDF document indicating date created of Nov. 21, 2007.
Thorlabs Inc., "Mounted Round Step Variable NDC Filter," Drawing No. 10664-E01, Part No. NDC-100S-4M, obtained from http://www.thorlabs.com/, PDF document indicating date created of Nov. 21, 2007.
Dudley, Dana, et al., "Emerging Digital Micromirror Device (DMD) Applications," DLP Products New Applications, Texas Instruments, Inc., obtained from http://www.loreti.it/Download/PDF/DMD/paper_dmd.pdf, PDF document indicating date created of Nov. 5, 2002.
Texas Instruments, "DMD Discovery 1100 Controller Board GUI User's & Programmer's Guide," Sep. 2004.

MULTI-CHANNEL DETECTOR ASSEMBLY FOR DOWNHOLE SPECTROSCOPY

BACKGROUND

This application is filed concurrently with application Ser. No. 12/613,700 and entitled "Multi-Channel Source Assembly for Downhole Spectroscopy", and with application Ser. No. 12/613,665 and entitled "Filter Wheel Source Assembly for Downhole Spectroscopy", which are both incorporated herein by reference in their entireties.

Background

Downhole tools use various types of sensors to test a downhole formation, analyze fluids, and perform other operations. Because the downhole environment has high temperatures, high pressures, harsh chemicals, and mechanical vibrations, the downhole tools must be mechanically designed to handle problems associated with such harsh conditions, and the downhole sensors must still be able to operate with analytical accuracy and reliability. Added to these challenges, the downhole sensors must fit in the limited space available in the downhole environment, must be light weight and power efficient, and must have a large dynamic range.

In the art, spectrophotometers, spectrometers, spectrofluorometers, refractive index analyzers, and similar devices have been used to analyze downhole fluids by measuring the fluid's spectral response. Each of these devices typically use some form of electromagnetic (EM) radiation to perform its function (i.e., to analyze the fluid). In general, the wavelengths of the EM radiation can be in the x-ray, gamma, ultraviolet, visible, infrared or any combination of these ranges. When the radiation is detected, the response can identify characteristics of the analyzed fluid, such as the type of fluid (e.g., oil, water, and/or gas), the level of filtrate contamination, the hydrocarbon composition (e.g., amount of methane (C1), ethane (C2), propane (C3), etc.), the gas-to-oil ratio (GOR), etc. Knowledge of these characteristics can then be employed to model the reservoir, plan production, and perform other tasks.

A number of optical devices have been developed in the art for spectral analysis. For example, small spectroscopes use LEDs and detectors. See Cantrell et al., "The SLIM Spectrometer," Analytical Chemistry, vol. 75, no. 1, pp. 27-35 (2003); See also Yeh et al., "Low Cost LED Based Spectrometer," Journal of the Chinese Chemical Society, vol. 53, pp. 1067-1072 (2006).

In another example, a spectrometer disclosed in U.S. Pat. No. 6,075,595 uses light emitting diodes (LEDs) for light sources and uses a detector for detection. The spectrometer can image the LEDs into a single optical channel, and the detector obtains the radiation pulses related to each LED in turn. See also Malinen et al., "LED-based NIR Spectrometer Module for Hand-Held and Process Analyser Applications," Sensors & Actuators B, vol. 51, no. (1-3), pp. 220-226 (1998). Thus, it appears that the spectrometer is not capable of synchronous detection.

In another example, a multi-wavelength photometer uses seven LEDs, 1-mm plastic optic fibers, a 7×2 coupler, and two photodiodes. See Hauser et al., "A Multi-wavelength Photometer Based on Light-Emitting Diodes," Talanta, vol. 42, no. 4, pp. 605-612 (1995). The two photodiodes can apparently correct for drift and intensity differences. In addition, the LEDs are illuminated one at a time so that the photometer does not appear capable of synchronous detection.

None of the above-described devices is suitable for use in a downhole environment. Moreover, each of the devices only offers a limited number of spectral channels for output and detection, which adversely affects both spectral resolution and range in detection and further makes these devices unsuitable for downhole use.

Other devices disclosed in the art can be used downhole. In U.S. Pat. No. 6,476,384 to Mullins et al., for example, a device has a broadband halogen lamp source and has a mechanical chopper wheel driven by a motor. The lamp is imaged into an optical fiber bundle, and light from the bundle is directed to a photodiode used to synchronize the chopper wheel's motor. A calibration wheel driven by a rotary solenoid switch selects whether light from the bundle passes into a first path, a second path, or both. In the first path, light is directed to a light distributor forming part of a detector. In the second path, light is provided as input to a measurement cell and is afterward directed to the light distributor for the detector. The light distributor distributes the light received from the paths to a number of different channels with each channel having a dedicated detection system (lens, filter photodiode). While this device's broadband source does provide a number of spectral channels, the device must use a mechanical chopper, cannot perform synchronous detection, and requires a complex spectral detection system consisting of multiple photodiodes (i.e., one per spectral channel).

In U.S. Pat. Nos. 7,336,356 and 7,379,180 to Vannuffelen et al., a device has a broadband source that may have a plurality of light sources. The device uses a rotating chopper wheel rotated by a motor to modulate the frequency of reference and measurement paths independently. For example, the measurement path has a first frequency and is split into two parts, and the reference path has a second frequency and is split into two parts. Each of these parts is then routed to multiple detection systems.

In US Pat. Pub. No. 2007/0109537, Vannuffelen et al. discloses an alternative approach that utilizes mechanical choppers and motors. Unfortunately, this approach, by design, is apparently limited to conventional raster scanning (CRS) spectroscopy, which involves scanning a plurality of sources or measurement wavelengths in a sequential fashion using a fixed time per channel (i.e. source or wavelength). As a consequence, CRS prevents synchronous detection of all spectral channels. Moreover, the device requires reference and measurement signals to be deconvolved from the response of a single detector. Because the signal convolution using a single mechanical chopper results in shared harmonics, the device uses dual mechanical chopper assemblies to circumvent the complication of shared harmonics. Although this may simplify signal de-convolution, it adds further complexity to the devices and raises concerns relative to space, mechanical reliability, and accuracy.

Another device for downhole analysis of fluids disclosed in US Pat. Pub. No. 2007/0013911 to DiFoggio et al. provides Wavelength Modulation Spectroscopy (WMS). The device uses a narrow light beam source and a tunable optical filter (TOF). In additional disclosures of U.S. Pat. Nos. 7,280,214 and 7,362,422, both electrically tunable filters and mechanically (i.e. rotating) tunable filters are used for WMS. As purported, WMS eliminates the need for a second spectral reference channel. However, the devices have limited spectral range, which limits their use for downhole analysis of fluids. Specifically, each filter, whether electrical or mechanical in nature, possesses a limited tunable spectral bandwidth. To increase spectral range, the device requires multiple narrow band sources and tunable filters, which is mechanically cumbersome for the downhole environment. In addition, the device uses a single channel detection system that prohibits synchronous detection because the tunable optical filters are actuated using a single motor assembly, which gives each spectral channel a common fundamental frequency. Thus, it appears that the device uses conventional raster scanning and is not capable of synchronous detection.

As disclosed in US Pat. Pub. No. 2008/0165356 to DiFoggio et al., another device has a laser diode array source containing a plurality of semiconductor light sources that enable conventional raster scanning (CRS) and Hadamard and synchronous Fast-Fourier Transform (FFT) scanning. However, the device lacks a way to dynamically scale the spectral response, and the device's sources lack a way for imaging a large number of spectral channels into a single spectral analyzer.

Therefore, in light of the above, what is lacking in the art is a downhole detection system that is ameanable for use with a broadband multi-channel source for downhole spectral analysis and that enables self-referencing, low-power operation, synchronous detection, and S/N improvement using discreet modulation of individual spectral channels.

SUMMARY

A multi-channel detector assembly can be used in a downhole tool to measure optical signals for downhole spectroscopy. The detector assembly has individual spectral detectors that measure optical signals across a spectral range of wavelengths. These detectors can be a single-element photodiode, a multi-element photodiode, an avalanche photodiode, a photomultiplier tube, a micro-channel plate, a bolometer, or a thermopile.

In particular, the assembly has a reference unit with at least one reference detector and has a measurement with at least one measurement detector. The reference unit is optically coupled to a reference channel of a source, and the at least one reference detector detects first spectral signals across a spectral range of wavelengths from the reference channel. The measurement unit is optically coupled to a measurement channel of the source, and the at least one measurement detector detects second spectral signals from the measurement channel after interaction with a fluid sample.

In one implementation, a plurality of reference detectors and measurement detectors can be used. For the reference detectors, a first router assembly partitions the reference channel into a plurality of first beams or spectral bands and routes each of the first beams to one of the reference detectors. Similarly, a second router assembly partitions the measurement channel into second beams or spectral bands for routing to each measurement detector. The routers can use one or more optical elements disposed in an optical path of the channel to partition the channel into two or more beams or spectral bands. The optical elements used can be high-pass filters, low-pass filters, dichroic elements, or an adaptive optical element.

Communicatively coupled to the reference and measurement detectors, conversion circuitry converts the first and second spectral signals into reference signals and measurement signals, and control circuitry communicatively coupled to the conversion circuitry processes these signals. In processing the signals, the control circuitry deconvolves the signals based on the type of encoding used to encode the spectral signals when output by the source. In general, the encoding can be based on Fast Fourier Transform (FFT) encoding, Hadamard encoding, temporal encoding, spectral encoding, or other type of encoding.

Because the assembly utilizes a dedicated reference channel, the control circuitry can process the measurement and reference signals from these channels to improve the operation of the source and to improve the detection capabilities of the detector assembly. To improve operation of the source, for example, the control circuitry can be operatively coupled to the source and can control output of spectral signals from the source based at least on the processed reference signals. Because the reference channel is a direct measurement of the source, the control circuitry can interrogate the source for fluctuations and/or weakness so that the control circuitry can thereby directly control the source's amplitude based on the reference channel. The control circuitry can also temporally sync the output of the spectral signals of the source with at least the first spectral signals detected by the reference detector and control the source and detection accordingly.

To improve detection, for example, the control circuitry can use the reference channel to dynamically scale any measurement channel. With this dynamic scaling, the control circuitry can account for fluctuations, drift, etc. in the source and can improve the signal levels in both channels. For example, the control circuitry can dynamically scale the measurement signal with the reference signal when processing the signals. The result of this scaling is a scaled measurement signal that already has real-time correction of variations in the measurement channel caused by disparate environmental responses, such as but not limited to temperature changes, drift in the source's operation, and drift in the detector assembly's electronics. In other words, the control circuitry scales the measurement channel with the reference channel so that the scaled measurement channel is essentially immune to disparate environmental responses.

In addition to these forms of control, the control circuitry can receive data of one or more environmental conditions from one or more external transducers. The control circuitry can then use the information from the external transducers as input to a scaling function or a lookup table employed to scale the processed measurement signal. This scaling can thereby account for spectral changes that would be caused by the environmental conditions detected by the transducers.

In configuring the source, the control circuitry can configure the modulated pulse train for illuminating the source by defining amplitude, start time, pulse frequency, duty cycle, pulse shape, or other temporal characteristic for the modulated pulse train. This modulated pulse train can then be used by the source to generate the output of spectral signals. Thus, the control circuitry having configured the source knows the modulated pulse train used, and the control circuitry mathematically deconvolves the detected spectral signals from the reference and measurement channels based on the known modulated pulse train configuration parameters provided by the source sync signal of the control circuitry.

The deconvolution uses a series of mathematical steps involving but not limited to mean centering, inverting, summing, and dynamic scaling. For example, by mean centering values of the pulse train, inverting the mean centered pulse train at unique temporal locations, and summing the inverted pulse train values, the control circuitry can determine a summed pulsed train value that can be directly correlated with an amplitude of the spectral signal. Ultimately, this correlation allows spectroscopic analysis to determine characteristics of the fluid interacting with the measurement channel. In addition to this form of deconvolution, optical signal deconvolution can utilize FFT or Hadamard mathematical transformations, each requiring a set of operational parameters specified by the control circuitry.

The foregoing summary is not intended to summarize each potential embodiment or every aspect of the present disclosure.

DETAILED DESCRIPTION

A. Downhole Tool Having Measurement Device for Fluid Analysis

Figure 1:
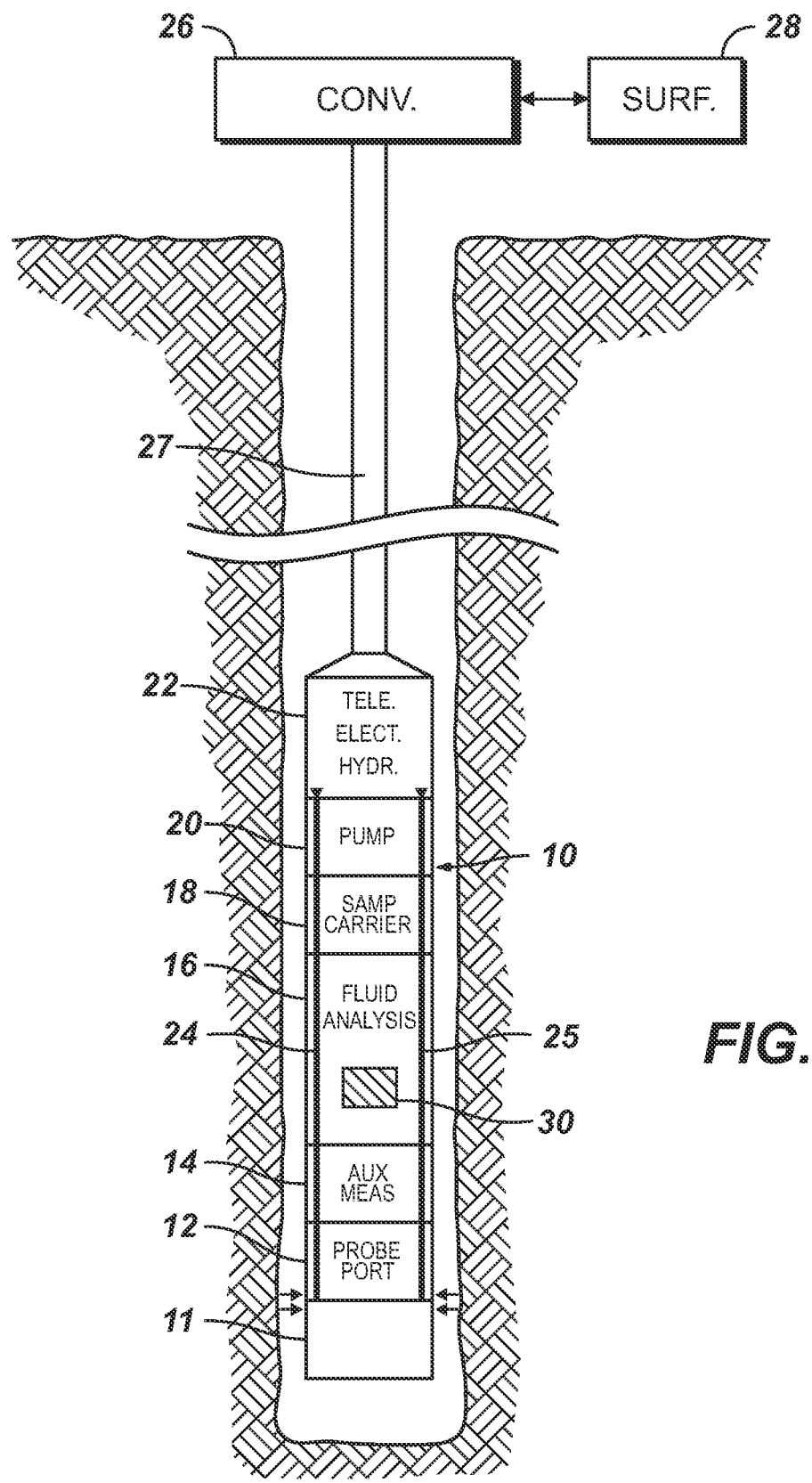
FIG. 1 illustrates a downhole tool having a measurement device for fluid analysis.

A downhole tool 10 in FIG. 1 has a measurement device 30 for in-situ sampling and analysis of fluids in a wellbore. A conveyance apparatus 26 at the surface deploys the tool 10 downhole using a tubular, a cable, a wireline, or similar component 27. As shown in FIG. 1, the tool 10 can be a formation tester such as disclosed in U.S. Pat. Pub. No. 2008/0173083, filed Jan. 24, 2007, which is incorporated herein by reference. However, the measurement device 30 can be deployed in any suitable tool used for wireline formation testing, production logging, Logging While Drilling/Measurement While Drilling (LWD/MWD), or other operations.

1. Downhole Tool

As shown in FIG. 1, the formation tester tool 10 has dual fluid flow lines 24/25 that extend through sections of the tool 10 and that are functionally configurable. However, other types of formation tester tools could also be used, such as those having a single flow line. In operation, a probe 12 having an intake port draws fluid into the tool 10. To isolate the formation fluid samples from contaminates in the annulus, the tool 10 can use isolation elements, such as packers 11 or other devices, to isolate a region of the formation.

A pump 20 then pumps collected fluid from the probe 12 into the tool 10 via the flow lines 24/25. The fluid, which can contain hydrocarbon components (solid, liquid, and/or gas) as well as drilling mud filtrate or other contaminants, flows through the tool 10, and various instruments and sensors in the tool 10 analyze the fluid. For example, a measurement section 14 can have sensors that measure various physical parameters (i.e., pressure, temperature, etc.) of the fluid, and the measurement device 30 in the fluid analysis section 16 can determine physical and chemical properties of oil, water, and gas constituents of the fluid downhole. Eventually, fluid directed via the flow lines 24/25 can either be purged to the annulus or can be directed to the sample carrier 18 where the samples can be retained for additional analysis at the surface.

Additional components 22 of the tool 10 can hydraulically operate valves and other elements within the tool 10, can provide control and power to various electronics, and can communicate data via wireline or fluid telemetry to the surface. Uphole, surface equipment 28 can have a surface telemetry unit (not shown) to communicate with the downhole tool's telemetry components. The surface equipment 28 can also have a surface processor (not shown) that performs additional processing of the data measured by the tool 10.

2. Measurement Device for Downhole Fluid Analysis

As noted above, the fluid analysis section 16 uses the measurement device 30 for downhole fluid analysis. Depending on the configuration and types of sources and detectors used and their orientation relative to a sample, the measurement device 30 can operate as a photometric analyzer, reflectometer, spectroscope, spectrophotometer, spectrometer, or the like. For example, the measurement device 30 can operate as a multi-channel photometric analyzer in which discrete wavelengths are interrogated over a given measurement range. In common usage, such a multi-channel photometric analyzer can be referred to as a spectrometer. Thus, the measurement device 30 can use various discrete spectral channels to perform spectroscopic analysis of downhole fluid passing relative to it as the fluid is pumped through the tool 10 (FIG. 1). As such, the spectroscopic analysis discussed herein can include, but may not be limited to, analysis of transmission, absorbance, fluorescence, or reflectance spectra, upon which chemometrics, derivative spectroscopy, and other techniques known in the art can be applied. Details of how a spectroscope can be implemented in a downhole tool are disclosed in U.S. Pat. No. 7,508,506, which is incorporated herein by reference.

Figure 2A:
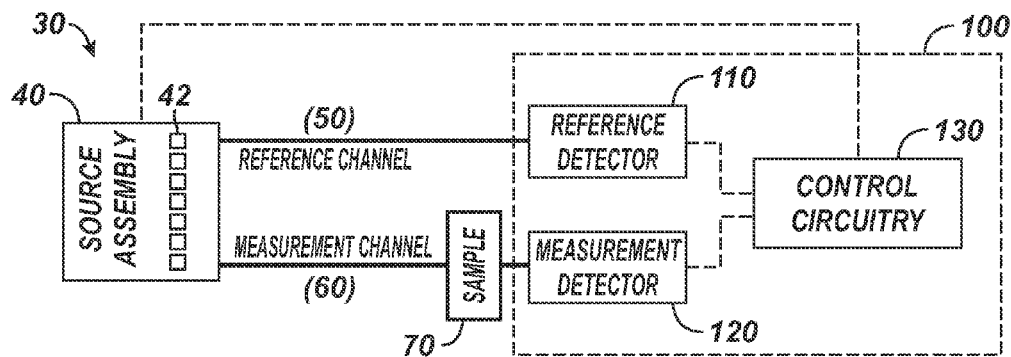
FIG. 2A schematically illustrates a measurement device for fluid analysis having a source assembly, a sample unit, and a detector assembly.

As schematically shown in FIG. 2A, the measurement device 30 has a source assembly 40, a sample interface assembly 70, and a detector assembly 100. The source assembly 40 can have one or more spectral sources 42, which can include broadband sources (e.g., tungsten halogen lamp, deuterium light source, xenon light source, coiled filament IR emitter, arc lamp, metal halide lamp, etc.) and solid state electronic sources (e.g., light emitting diode (LED), super-luminescent light emitting diode (SLED), laser diode (LD), etc.). In one implementation, the source assembly 40 can be an assembly as disclosed in incorporated application Ser. No. 12/613,700 and entitled "Multi-Channel Source Assembly for Downhole Spectroscopy" or as disclosed in incorporation application Ser. No. 12/613,665 and entitled "Filter Wheel Source Assembly for Downhole Spectroscopy."

The source assembly 40 generates spectral signals partitioned into two channels—a reference channel 50 and a measurement channel 60. The reference channel 50 travels directly to the detector assembly 100. The measurement channel 60, however, interacts with a sample fluid via the sample assembly 70 and then travels to the detector assembly 100. In turn, the detector assembly 100 includes a reference detector unit 110 for the reference channel 50, a measurement detector unit 120 for the measurement channel, and control circuitry 130 coupled to these units 110/120. Although one measurement channel 50 is shown along with one reference channel 60, it will be appreciated that multiple measurements channels 50 can be provided for the same reference channel 60. Therefore, the device 30 can have several measurement channels 50 along with sample assemblies 70 and detector units 80 for separate analysis.

Figure 2B:
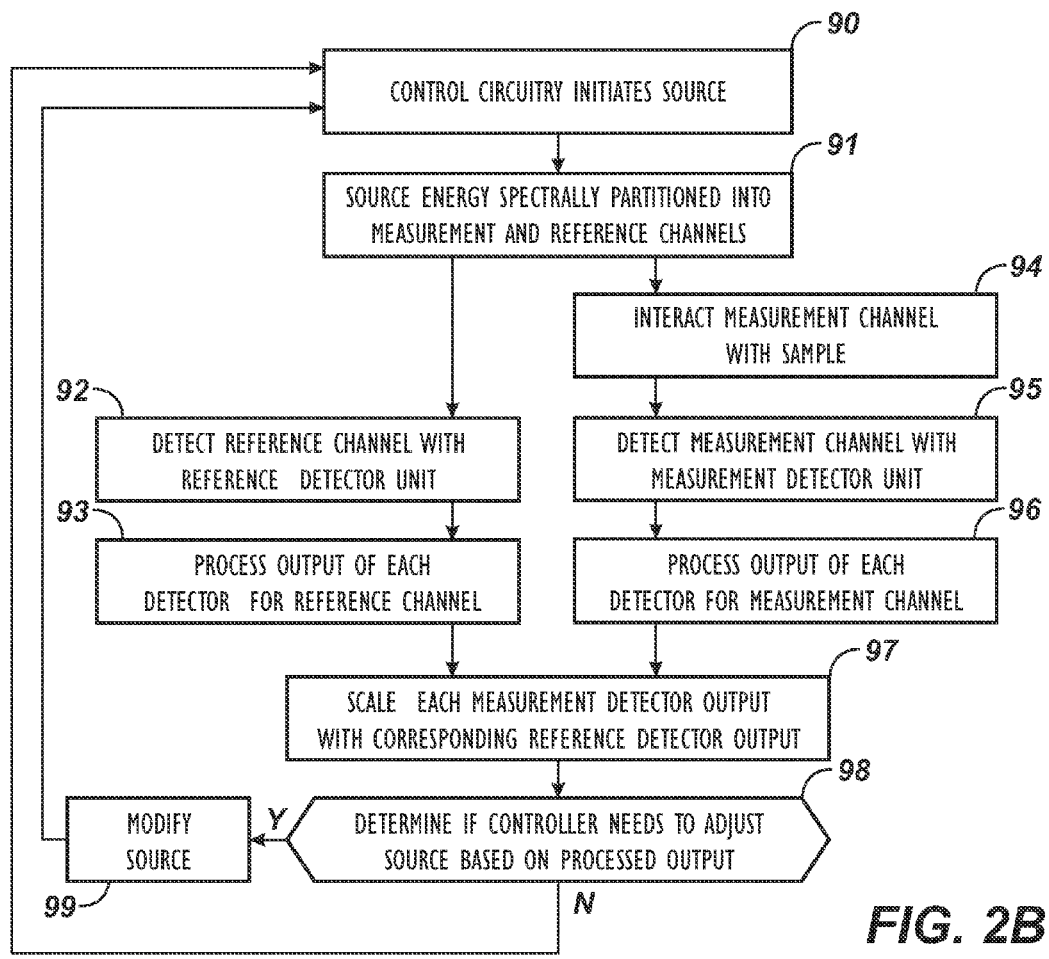
FIG. 2B shows the general operation of the measurement device shown in FIG. 2A.

One operational scheme of the measurement device 30 is discussed concurrently with reference to FIG. 2B. The detection control circuitry 130 initiates the source assembly 40 so that the source assembly 40 generates source energy (i.e., spectral signals of EM radiation) with its one or more sources 42 (Block 90). To initiate the source assembly 40, the control circuitry 130 can trigger source control circuitry (not shown) of the assembly 40, define operational parameters for the source assembly 40, or perform some other form of interaction with the assembly 40 (Block 90). For example, the control circuitry 130 can control the source assembly 40 by operating the spectral sources 42 using a specific set of operating parameters (start time, frequency, duty cycle, etc.). The operating parameters specify the encoding of the optical sources facilitating signal processing after detection. When generating the spectral signals, for example, the source assembly 40 can encode the signals using Conventional Raster Scanning (CRS), Fourier Transform (FT), or other encoding technique for spectroscopic analysis.

After generating the signals, the source assembly 40 routes or spectrally partitions the generated signals into the reference channel 50 and measurement channel 60 (Block 91). For example, the source assembly 40 can create a first optical path constituting a first fraction or minority of the generated signals to be used as the reference channel 50 and can create a second optical path constituting a second fraction or majority of the generated signals to be used as the measurement channel 60. In one implementation, the measurement channel 60 constitutes 90% of the generated signals, while the reference channel 50 constitutes 10% of the generated signals, although other percentages could be used in other implementations. Throughout this disclosure, these channels 50/60 or light paths are referred to as a "measurement channel" and a "reference channel" to indicate that the measurement channel 60 interrogates a sample with EM radiation while the reference channel 50 is used for dynamic referencing or other purposes disclosed herein.

The spectral signals of the measurement channel 60 interact with a sample via the sample unit 70 (Block 94). For its part, the sample assembly 70 can use different designs, including, but not limited to, a sample cell, a reflectance accessory, a transmittance accessory, a fluorescence accessory, an Attenuated Total Reflectance (ATR) accessory, an extractive flow cell, or any other sampling or monitoring device known to those skilled in the art.

The reference and measurement channels 50 and 60 are collected by the detector units 110 and 120, respectively (Block 92/95). For example, the reference detector unit 110 detects the spectral signals and sends detected reference signals to the control circuitry 130 (Block 92). In detecting these signals, the reference detector unit 110 can detect one or more spectral bands using one or more spectral detectors as detailed below. After interaction with the sample, for example, the measurement detector unit 120 detects the spectral signals and sends detected measurement signals to the control circuitry 130 (Block 95). As with the reference detector unit 110, the measurement detector unit 120 can detect one or more spectral bands with one or more detectors.

At this point, the control circuitry 130 processes the output of the one or more detectors for the channels 50/60 (Block 93/96) and scales, if necessary, the output of each measurement detector using the corresponding reference detector signal (Block 97). This dynamic scaling can account for source anomalies due to downhole environmental conditions, aging, or the like. Once processed and scaled, the processed signals provide information that can be used to correlate the spectral response with specific fluid properties and characteristics, and the resulting spectral data can be used to determine chemical and/or physical properties of the sample fluid. This can be performed by the control circuitry 130 itself or by some other controller. Ultimately, as referenced above, the measurement device 30 of FIG. 1 can transmit spectral data to a processing system (not shown) located on the tool 10 or at the surface equipment 28.

At some point during processing, the control circuitry 130 determines if the output of the source assembly 40 needs to be modified (Decision 98). If no modification is necessary, operation continues using the operating parameters originally specified. If modification is necessary, however, the source assembly 40 is re-initiated with a new set of operational parameters (Block 99). For example, the source(s) 42 in the source assembly 40 may be operated using pulse width modulation, and the control circuitry 130 can configure a modulated pulse train used to operate the sources 42 with specific characteristics, such as modulation amplitude and frequency. In such an instance, the control circuitry 130 may modify the source assembly's output by signaling the source assembly 40 to make a necessary adjustment or by configuring and supplying temporal characteristics for the pulse train to be used by the source assembly 40 in generating the spectral signals (Block 99). In general, these pulse train temporal characteristics can include, but are not limited to start time, pulse frequency, duty cycle, and pulse shape.

B. Downhole Multi-Channel Detector Assembly

With an understanding of the measurement device 30 and the downhole tool 10 in which it can be deployed, discussion now turns to different arrangements of a multi-channel detector assembly 100 for downhole spectroscopy according to certain teachings of the present disclosure.

1. Single Detector Arrangement

Figure 3:
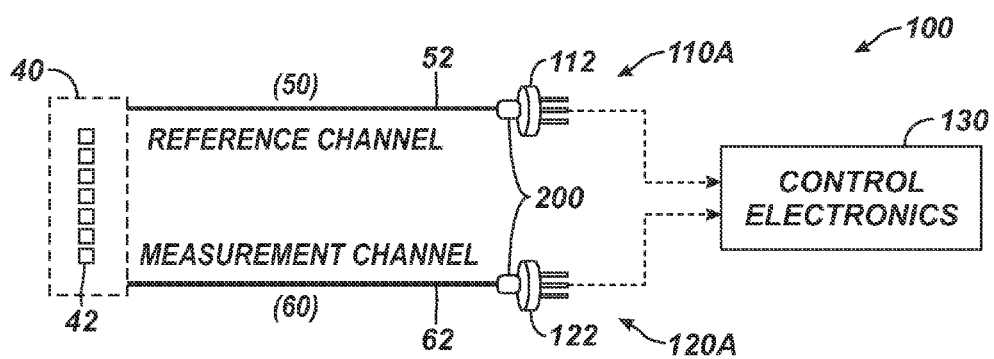
FIG. 3 schematically illustrates the detector assembly having single detector units.

In a first arrangement shown in FIG. 3, the multi-channel detector assembly 100 is set up with a single detector arrangement for each channel 50/60. As shown, the detector units 110A/120A each have a single detector 112/122 for detecting one beam or band of spectral energy from their respective channel 50/60. In general, the detectors 112/122 in the units 110/120 can use any of the various available configurations (i.e., single or multiple element photodiodes (PD), avalanche photodiodes (APD), photomultiplier tubes (PMT), Multi-Channel Plates (MCP), bolometers, thermopiles, etc.) and can have a sensing substrate composed of Si, SiC, InGaAs, InAlGaAs, Pbs, PbSe, or any other known material for sensing spectral radiation. For example, the detectors 112/122 can be photodiodes capable of sensing in the near infra-red (NIR), ultraviolet (UV), and/or visible (Vis) spectrum, or in some other spectral range depending on the implementation.

In operation, the detectors 112/122 detect spectral signals from the channels 50/60 in the specific band used, and the control circuitry 130 receives the output from the detectors 112/122 for processing and analysis. As noted above, for example, the reference channel 50 can then be used as optical feedback for controlling the source assembly (40) and/or to dynamically scale the spectral signal of the measurement channel 60.

Figure 4A:
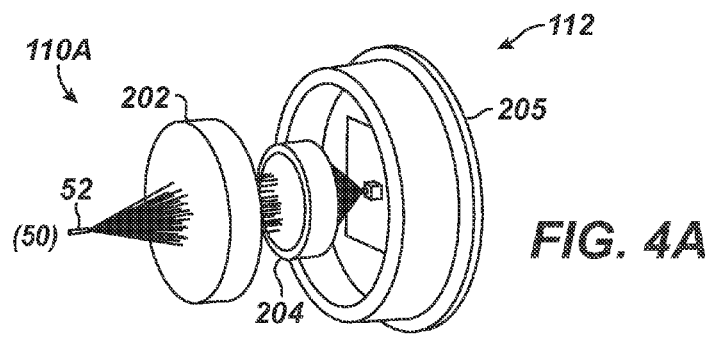
FIGS. 4A-4B illustrate exploded views of a fiber coupling to a detector for the single arrangement of FIG. 3.
Figure 4B:
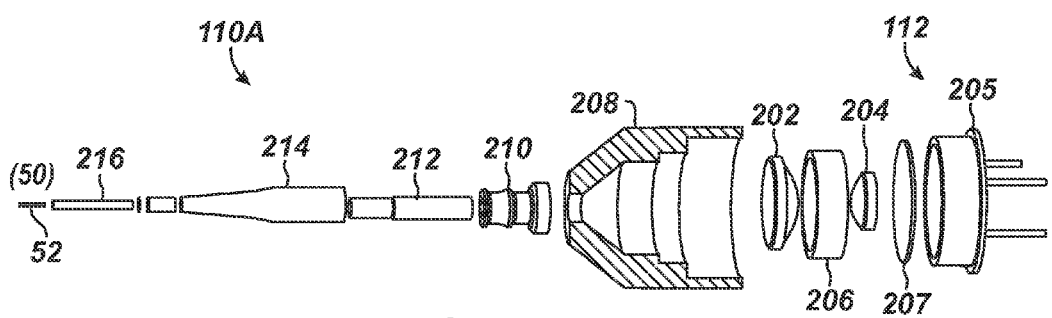

In general, the spectral signals of each channel 50/60 can pass through free space using a series of discrete optical elements in a non-fiber based arrangement. Alternatively as shown, the spectral signals of each channel 50/60 can be carried from the source assembly (40) by a fiber optic cable 52/62 and imaged onto the detector 112/122 using an optical coupling 200. In FIGS. 4A-4B, a representative optical coupling 200 is shown that can be used in this arrangement. This coupling 200 images a fiber optic cable 52 onto a single photodiode of detector 112 (shown here for the reference channel 50). A collimating lens 202 and a focusing lens 204 position in a lens housing 208 separated by a lens spacer 206. The housing 208 with lenses 202/204 attaches to the photodiode of detector 112, which has a header 205 and a window 207. On the other end, a fiber-ferrule assembly 210, strain relief boot 212, ferrule mounting tube 214, and alignment sleeve 216 couple the fiber 52 to the housing 208. It will be appreciated that, besides this optical coupling 200, other fiber and non-fiber-based arrangements could be used to image the spectral signals from the channels 50/60 onto the detectors 112/122.

2. Dual Detector Arrangement

Figure 5:
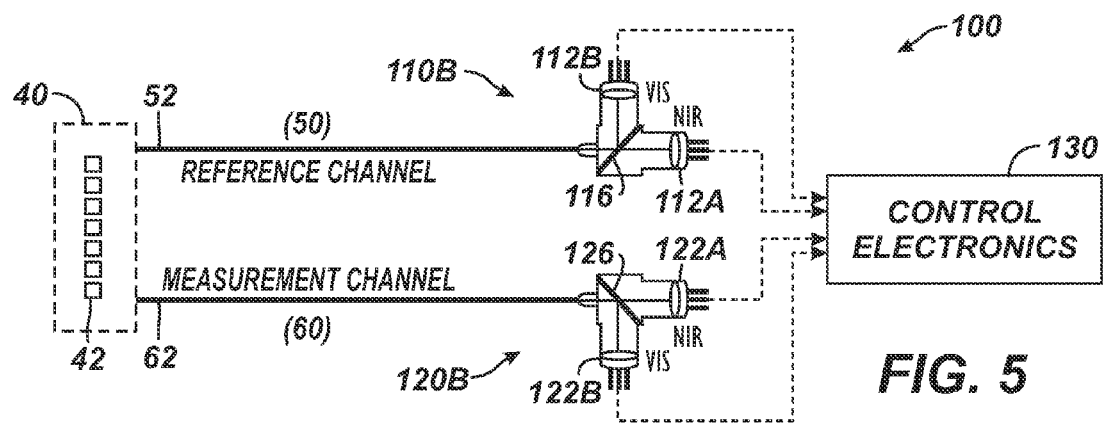
FIG. 5 schematically illustrates the detector assembly having dual detector reference and measurement units.

In a second arrangement shown in FIG. 5, the multi-channel detector assembly 100 is set up with a dual detector arrangement for the reference and measurement channels 50/60. As shown, each detector unit 110B/120B has dual detectors 112A-B/122A-B for detecting two beams or bands of spectral energy from their respective channels 50/60. For example, first detectors 112A/122A can be photodiodes capable of sensing in the near infra-red (NIR) spectrum, while second detectors 112B/122B can be photodiodes capable of sensing in the ultraviolet (UV)/visible (Vis) spectral ranges, although other spectral ranges could be used. In combination, each dual band detector unit 110B/120B can detect a wavelength range of about 350 to about 2400-nm, for example.

A router assembly inside each dual band detector unit 110B/120B partitions the spectral signals of the channels (50/60) into separate or different beams or bands and routes those beams or bands to individual detectors. (In general, there may be some overlap between the spectral bands in the two beams.) Inside each unit 110B/120B, for example, a high pass beam splitter 116/126 splits the incoming channel (50/60) into a first (NIR) band and a second (UV-Vis) band by reflecting all wavelengths shorter than a cutoff wavelength and by passing all longer wavelengths, or vice versa. In one implementation, the cutoff wavelength of the splitter 116/126 can be between 900 and 1000-nm. In general, the splitter 116/126 can be a dichroic element (e.g. mirror), a high pass filter, a low pass filter, a partial metalized mirror, or any optical elements known in the art that can partition the spectral signals into discrete spectral bands.

Once the channels (50/60) are split into bands, the first (NIR) detectors 112A/122A detect the first isolated bands passing through the splitters 116/126. These first (NIR) detectors 112A/122A can be InGaAs photodiodes used for sensing the NIR wavelength range, for example. Likewise, the second (VIS) detectors 112B/122B detect the second isolated bands from the splitters 116/126. These second (VIS) detectors 112B/122B can be silicon-based photodiodes used for sensing the visible and/or ultraviolet wavelength range, for example. After detection, the control circuitry 130 coupled to each of the detectors 112A-B/122A-B interrogates the detectors' responses for processing and analysis.

Figure 6A:
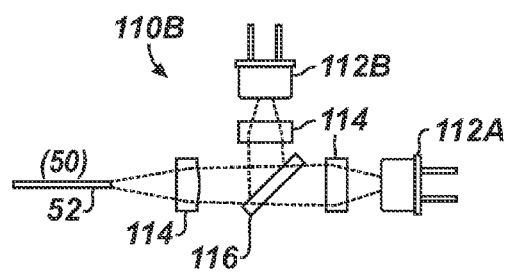
FIGS. 6A-6C illustrate fiber-based routers for the dual detector units of FIG. 5.
Figure 6B:
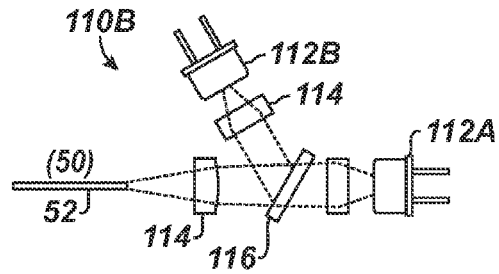
Figure 6C:
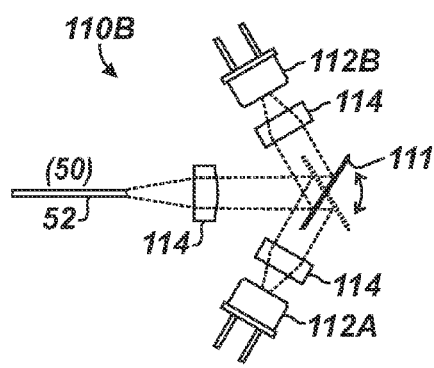

FIGS. 6A-6C show embodiments of a dual detector unit 110B for the reference channel (50) in more detail, although some of the surrounding components for housing the unit's elements are not shown for simplicity. (The dual detector unit 120B for the measurement channel can be similarly configured.) A fiber optic cable 52 carriers the spectral signals of the reference channel (50), and a router assembly having lens optics 114 and splitter 116 partitions the signals and routes separate or different bands to the dual detectors 112A-B. In particular, a first lens optic 114 collimates the signal from the fiber optic cable 52. The collimated signal passes to the splitter 116 that splits the energy into the two bands, one for the first detector 112A and another for the second detector 112B. Additional lens optics 114 then image the separate or different bands to the photodiode dies of the detectors 112A-B. As shown in FIG. 6A, the detectors 112A-B can be arranged perpendicularly. Alternatively, they can be arranged at an acute angle as in FIG. 6B.

In FIG. 6C, the dual band detector unit 110B for the reference channel (50) has a router assembly with an adaptive optic element 111 for partitioning the reference channel (50). As before, fiber optic cable 52 carriers the spectral signals of the reference channel (50), and the router assembly has a lens optic 114 that collimates the signal from the fiber optic cable 52. At this point, the router assembly uses its adaptive optic element 111 that oscillates between two or more orientations to partition the input signals into separate beams alternatingly routed to the dual detectors 112A-B. The adaptive optic element 111 can be a scanning mirror, such as a micro-electromechanical (MEM) mirror device or a Micro-Electro-Mechanical System (MEMS) scanning mirror.

A first beam reflected from the element 111 passes to a first lens optic 114 that images the beam to the first detector 112A, and a second beam reflected from the element 111 passes to a second lens optic 114 that images the beam to the second detector 112B. One benefit with the arrangement in FIG. 6C is that there is no optical loss due to a beam splitter. Consequently, all optical energy in the system may be transmitted to each detector 112A-B. With the configuration shown in FIG. 6C, it is also easy to envision having multiple measurement channels and a single reference channel.

In one implementation, the two beams from the adaptive optic element 111 can be the same bands (i.e., can have the same spectral range of wavelengths), and the lens optics 114 for the separate detectors 112A-B may be filters filtering different wavelengths in the common spectral range. In another implementation, the adaptive optic element 111 can have a grating on its surface so that different spectral bands are reflected from the element 111 at different angles. In this way, one of the beams reflected from the grated element 111 can have one specific spectral range for the first detector 112A that is different than that for the second detector 112B.

Figure 7:
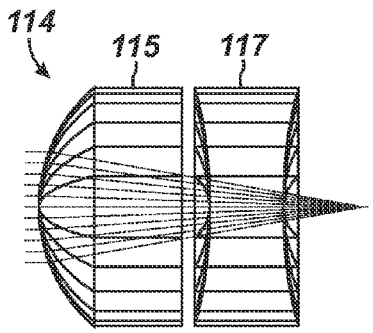
FIG. 7 shows an exemplary lens optic for the routers of FIG. 6A-6C.

In general, the lens optics 114 of FIGS. 6A-6C can be an achromatic lens, an achromatic lens pair, a plano-convex lens optically coupled to a bi-convex lens, etc. FIG. 7 shows an exemplary lens optic 114 that can be used for the routers disclosed herein. The lens optic 114 is a type of achromatic lens having a plano-convex (PCX) lens 115 and a bi-concave lens 117, which can have a physical separation using a spacer (not shown) or which can be cemented together using a suitable optically transmissive cement. The optical cement used must be able to withstand downhole operating temperatures. The material types and forms of the two lenses 115/117 are chosen to have offsetting focal length effects. Thus, as wavelength varies, the focal length of the bi-concave lens 117 changes more rapidly than that of the plano-convex lens 115.

This disparate change in focal length with wavelength serves to reduce the overall dependence of the combined focal length over a range of wavelengths.

Figure 8:
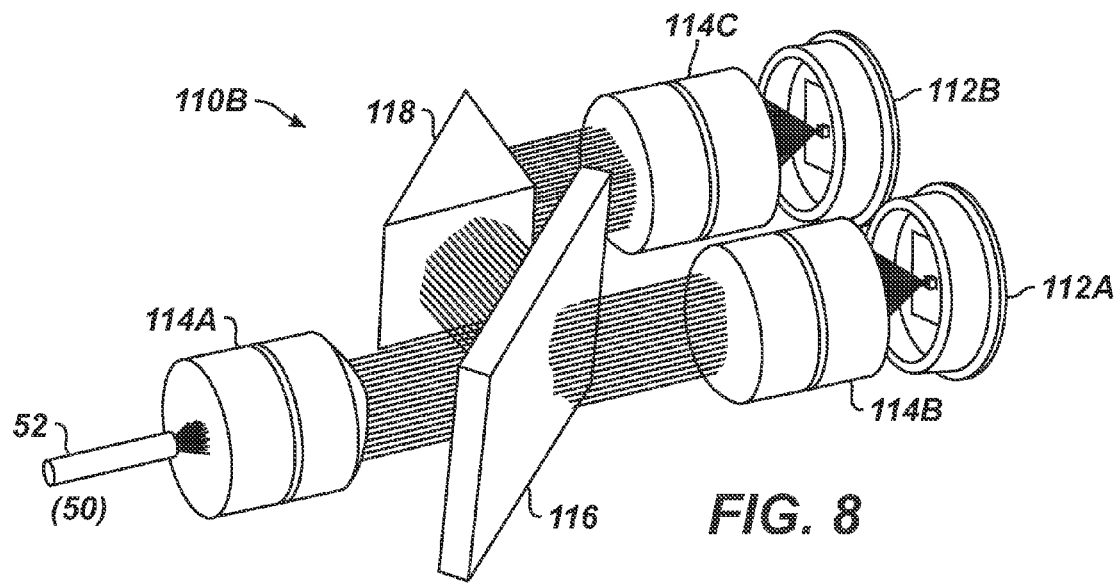
FIG. 8 shows a router for the dual detector unit having the lens optic of FIG. 7 and having a reflector.

FIG. 8 shows a dual band detector unit 110B for the reference channel (50) using the exemplary lens optic 114 of FIG. 7. In the router assembly, an input lens optic 114A receives the spectral signal from the fiber optic cable 52 for the reference channel (50), and the optic 114A collimates the signal. The splitter 116 then splits the collimated signal into the two bands as described previously, allowing longer wavelengths to pass through the splitter 116 and reflecting shorter wavelengths. One band passing from the splitter 116 reaches another lens optic 114B, which condenses the signal and images it onto the die of the first (NIR) detector 112A. The other band reflected from the splitter 116 reaches a reflector 118.

Although shown here as a right angle prism, the reflector 118 can be a mirror or other comparable optical element. The reflector 118 directs this band to another lens optic 114C, which condenses the signal and images it onto the die of the second (UV/Vis) detector 112B. The reflector 118, therefore, allows both bands to run parallel to one another and allows the two detectors 112A-B to be packaged together. Not only does this conserve space, which is important in a downhole tool, but being able to package the two detectors 112A-B together enables them to be arranged co-planar to one another and to experience the same environmental changes, such as the same overall thermal conditions.

3. Multi-Detector Arrangement

As discussed above, the detector assembly 100 in FIG. 3 represents a single detector arrangement capable of sensing in one band or spectrum, e.g., near infra-red (NIR) or ultraviolet (UV)/visible (Vis) spectral ranges, while the detector assembly 100 in FIG. 5 represents a dual detector arrangement that can simultaneously measure and reference in two bands or spectral ranges, e.g., the UV-Vis and NIR ranges. As noted previously, the dual detector units 110B/120B can be used to cover a measurement range of interest from about 350-nm to about 2400-nm. However, additional detectors could also be included in the unit 110B/120B to either further partition the range into discrete bands or to extend the range to cover a wider spectral range, such as from about 200-nm to over 3000 nm.

Figure 9A:
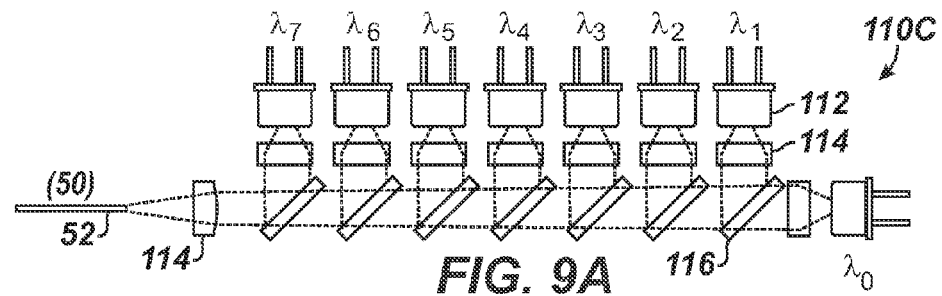
FIGS. 9A-9B illustrate additional routers for multi-detector units.

In FIG. 9A, for example, a multi-detector unit 110C has a router assembly with a series of low pass filters 116 that filter the spectral signals from the reference fiber optic cable 52 in stages of beams or bands to a series of reference detectors 112. Again, lens optics 114 image the collimated signals to the diode dies of the detectors 112. Because low pass filters 116 are used, the various combinations of detectors 112 and low pass filters 116 can decrease in wavelength ($\lambda_7-\lambda_0$) as they are positioned further away from the fiber optical cable 52 so that shorter wavelengths (higher frequencies) will reach further detectors 112. A reverse arrangement could also be used in which a series of high pass filters (as opposed to low pass filters) are used, and the combination of detectors 112 and high pass filters 116 can increase in wavelength ($\lambda_0-\lambda_7$) as they are positioned further away from the fiber optic cable 52 so that longer wavelengths (lower frequencies) will reach further detectors 112.

Figure 9B:
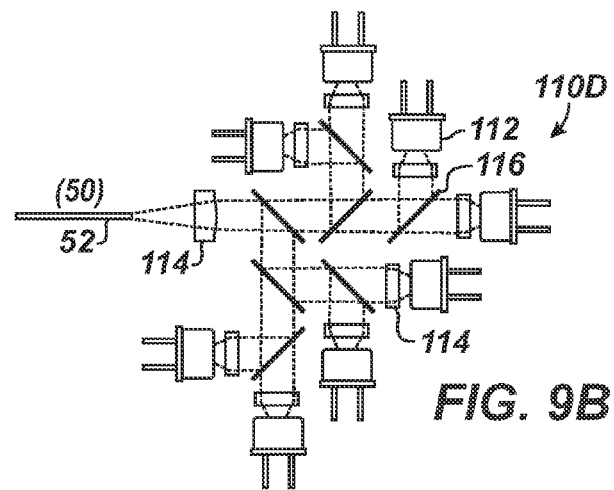

In addition to the above arrangements, FIG. 9B shows a multi-detector unit 110D having multiple detectors 112, lenses 114, and filters 116 having a clustered router arrangement. The filters 116 direct and split off wavelengths of interest from the reference fiber optic cable 52 to the various detectors 112 in a similar way to that discussed previously, but with a more compact arrangement that limits the number of filter passes per spectral band.

C. Housing Arrangements for Multi-Channel Detector Assembly

Because the detector assembly 100 is used downhole, housing its components can be constrained by the available tool space and the downhole environmental specifications. Ideally, components of the detector assembly 100 have a housing that is amenable to downhole deployment and that can fit into the tight downhole space required in a downhole tool. Therefore, the detector assembly 100 is preferably constructed as a discrete modular unit that can be incorporated or connected to other modular units, such as modular units for the source assembly (40) and sample assembly (70) in a downhole tool.

Because multiple detectors 112/122 are used and are subject to potentially changing environmental parameters such as temperature, the particular detectors 112/122 used are preferably mapped to determine how changes in their responsivity occur as a function of changes in environmental parameters. This mapping can then be used to match the detector's responsivity during use downhole to the real-time environmental changes occurring during operation. This enables the use of multiple detectors 112/122 despite the fact that such a multiple detector approach has been viewed as impractical in the art due to variations in detector-to-detector responsivity and operation. Ideally, the detectors 112/122 are also preferably super-matched to further reduce the detector-to-detector differences in environmentally induced responsivity and are preferably co-packaged in a single housing to reduce electronic and mechanical packaging complexity.

D. Control Circuitry

Figure 10:
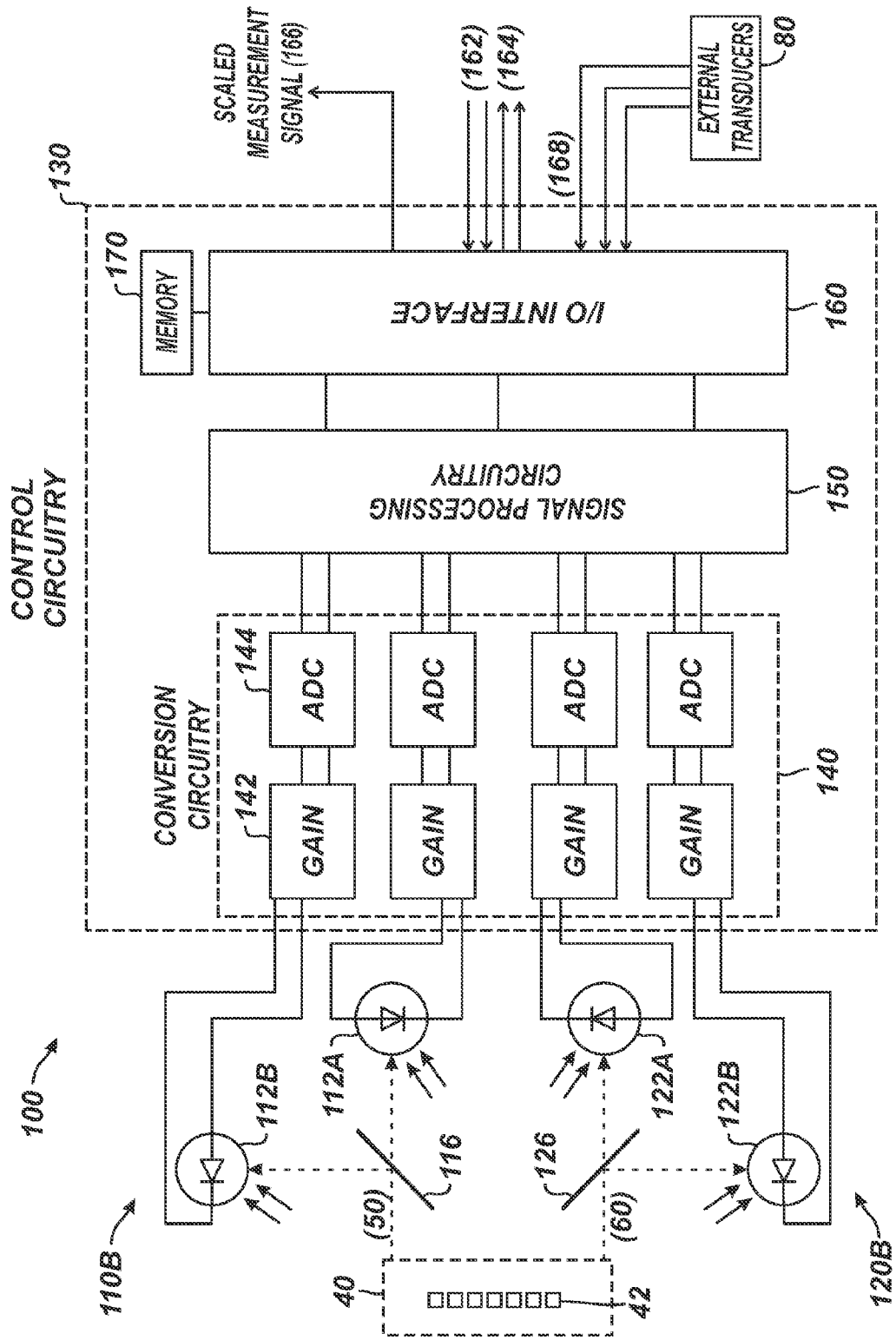
FIG. 10 schematically illustrates control circuitry for the disclosed detector assembly having a dual detector reference and measurement unit arrangement.

The multi-channel detector assembly 100 is schematically shown in more detail in FIG. 10, illustrating additional components of the control circuitry 130. As shown, the control circuitry 130 has conversion circuitry 140, signal processing circuitry 150, and an input/output interface 160. The conversion circuitry 140 connects to the detector units 110B/120B. The signal processing circuitry 150 receives detected signals from the conversion circuitry 140 and connects to the interface 160. In turn, the interface 160 connects to external transducers 80 through inputs 168 and connects to other components of the measurement device using digital and analog inputs/outputs 162/164. The interface 160 can also connect to suitable memory 170.

The detector units 110B/120B shown here are for the dual band arrangement. Therefore, the reference detector unit 110B has dual detectors 112A-B, and the measurement detector unit 120B has dual detectors 122A-B. Splitters 116/126 split the reference and measurement channels 50/60 into the two bands for the detectors 112A-B/122A-B as discussed previously. The conversion circuitry 140 receives the detected signals from the detectors 112A-B/122A-B and digitizes the detected analog signals for each channel 50/60.

To handle the analog signals from the detectors 112A-B/122A-B, the conversion circuitry 140 has gain circuits 142 that can include photodiode detector circuitry, analog filters, and amplifiers for each of the detectors 112A-B/122A-B. The gain circuits 142 can use a nominally zero bias photovoltaic operation and can be configured to handle various sources of noise, such as signal shot noise, dark current shot noise, shunt resistance thermal (Johnson) noise, etc.

From the gain circuits 142, the analog detector signals pass to analog-to-digital conversion (ADC) circuitry 144 that converts the analog detector signals into digital signals for the signal processing circuitry 150 to process. For this dual band arrangement, the ADC circuitry 144 can use four A/D conversion inputs with two inputs for the two reference channel bands from the reference detectors 112A-B and two inputs for the two measurement channel bands from the measurement detectors 122A-B. The multiple A/D conversion inputs of the circuitry 144 can be part of an integrated chip (IC) (i.e., a 4, 8, or 16 channel A/D) or can utilize multiple single channel A/D's. When using frequency modulation, the A/D conversion speed is preferably at least 8 times the maximum modulation frequency used to encode the spectral signals to ensure proper sampling.

After the ADC circuitry 144 converts the analog detector signals to digital signals, the signal processing circuitry 150 receives the digital signals and uses programmable control schemes to process the signals (i.e., to compare the signals for the two channel (50/60), to compare the signals for each channel's bands, to control operation of the assembly 100, to perform spectral data analysis, to package data for up-hole communication, etc.). Using the digital signals, for example, the signal processing circuitry 150 performs digital filtering (lock-in detection), absolute value conversion, RC filtering, averaging of the raw intensity signals, and/or Fast-Fourier Transform or similar de-convolution techniques, among other functions. In general, the signal processing circuitry 150 can have a microprocessor or Field-Programmable Gate Array (FPGA) and other appropriate electronics.

After processing the signals, the control circuitry 130 can store information in memory 170 and can communicate information to other components (e.g., source assembly (40), another controller, telemetry unit, etc.) using the input/output interface 160 and any of the various known techniques. In general, the control circuitry 130 can communicate processed information uphole in real-time as one or more data sets that include all raw data, partial raw data, averages, and the like. In one example, the control circuitry 130 can communicate an average raw intensity from both the measurement and reference detectors units 110B/120B in the separate bands (NIR and UV/Vis). Transmitting both of these data sets uphole allows operators at the surface to review each data set, thereby enhancing diagnostic capabilities for setting data integrity flags. In another example, the control circuitry 130 can communicate processed signal data, such as ratios. In this way, only a single data set needs to be transmitted. Regardless of how data is communicated, processing equipment at the surface can analyze the data and convert the data into unique values.

In general, the control circuitry 130 can operate as a standalone controller that communicates (sends and receives) triggers with the source assembly (40), which can have its own controller, so that the control circuitry 130 can coordinate its operation with that of the source assembly (40). Alternatively, the control circuitry 130 can implement direct control of the source assembly (40) by actually configuring some of the source assembly's operational parameters and sending control signals, parameters, and/or triggers to the source assembly (40) to implement. In yet additional alternatives, the source assembly (40) may actively control the detector assembly 100 by configuring some of its operational parameters, or an entirely separate controller can control both the source assembly (40) and the detector assembly 100.

As shown, the input/output interface 160 has inputs 162 and outputs 164 that can be analog and digital and has a scaled signal output 166 and inputs 168 for external transducers 80. The interface 160 can be used for triggering and external control of other control components, such as a controller of the source assembly (40; FIG. 2A). The interface 160 can also receive control signals used for manual or automated control of the circuitry's operation. This external control can be from an external source, such as a controller of the source assembly (40), surface equipment, or from a separate downhole controller. When received, the control signals can configure the control circuitry 130's operation to account for variable conditions, such as a change in temperature, a change in fluid to be analyzed, a change in desired mode of operation to be used, etc. The external control can also operate the control circuitry 130 to handle events that require exact timing by using the digital inputs and outputs 162/164 for triggering signals.

E. Measurement Device and Source Arrangement

Figure 11:
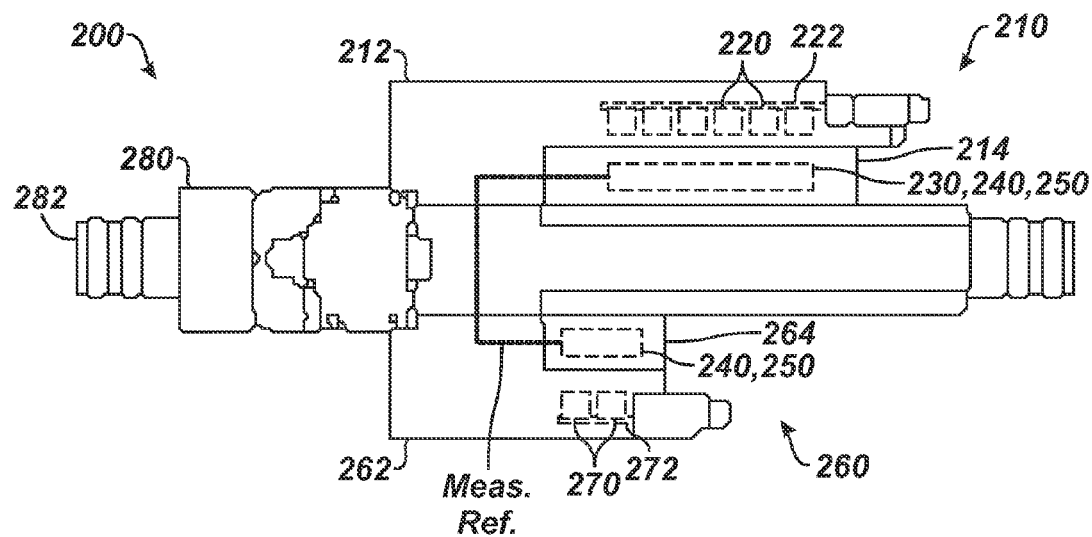
FIG. 11 illustrates a side view of a measurement device having a multi-channel source assembly and a detector unit.

In FIG. 11, a side view of a measurement device 200 has a multi-channel source assembly 210 and a detector assembly 260 disposed on a flow body 280. For use in a downhole tool, the flow body 280 fits onto a tool chassis (not shown) that holds the flow body 280 in place and holds required electronics. In turn, the flow body 280 mates with a subassembly (not shown) that routes the flow buses in the downhole tool, and the tool chassis fits inside a tool housing (not shown) of the downhole tool. Fluid from one of the tool's fluid buses passes through a passage 282 from one end of the flow body 280 to the other and passes by the source assembly 210 and detector assembly 260.

As shown, the source assembly 210 can have housings 212/214 that couple to the flow body 280. One housing 212 holds the LED sources 220 arranged on a circuit board 222. The other housing 214 holds an arrangement of beam splitters and prisms (230, 240, 250).

For its part, the detector assembly 260 can be similarly configured on the opposite side of the flow body 280. Accordingly, one housing 262 attached to the flow body 280 houses the photodiode detectors 270 disposed on a circuit board 272. Also, another housing 264 houses an arrangement of beam splitters and prisms (240, 250), which are detailed below in FIG. 12.

Signals for the measurement and reference channels issue from the source assembly 210 and pass to the detector assembly 260 using through-space optical elements (not shown). The reference channel can pass directly to the detector assembly 260, and the measurement channel can interact with fluid passing through the flow body 280 before passing to the assembly 260. Thus, the measurement channel may pass through a sample accessory (not shown), such as a sample cell or the like, in the flow body 280.

Figure 12:
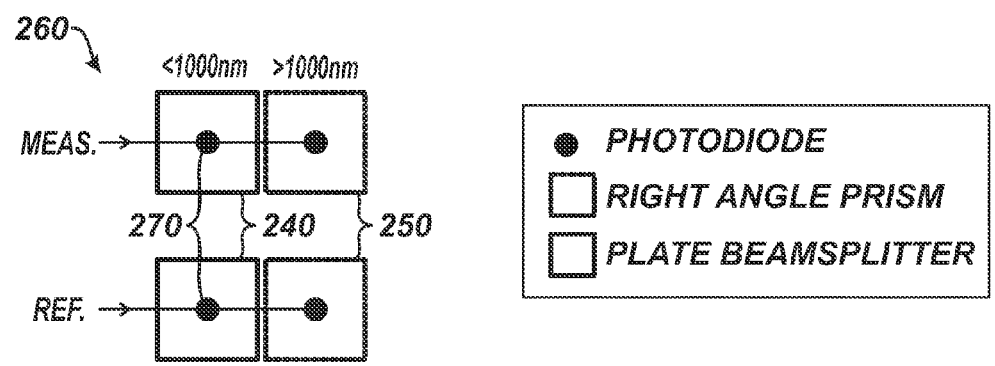
FIG. 12 diagrammatically illustrates arrangements for the source assembly and the detector units of the device in FIG. 11.

Turning then to the plan schematic view in FIG. 12, both channels can be routed via fiber, mirrors, and the like to the detector assembly 260. For example, through-space optical and fiber routing approaches known to those in the art or disclosed herein can be used to route the channels to the detector assembly 260. First photodiode detectors 270 receive the reference channel and have a plate beamsplitter 240 and right angle prism 250. Likewise, second photodiode detectors 270 receive the measurement channel and similarly have a plate beamsplitter 240 and right angle prism 250.

As shown, the detector assembly 260 has two photodiode detectors 270 for each channel with one detector 270 receiving wavelengths <1000-nm and the other receiving wavelengths >1000-nm. The plate beamsplitters 240 can have a cut-on wavelength intermediate to the detector ranges and either transmit above the cut-on or reflect below the cut-off. These details are meant to be merely exemplary, as one skilled in the art will appreciate that the number of detectors 270 and beamsplitters 240 as well as the subject wavelengths and other values can be configured for a particular implementation.

F. Dynamic Referencing

Being deployed downhole, the measurement device (30; FIG. 2A) can exhibit sensitivities to environmental stresses. However, the detector assembly 100 spectrally correlates the reference and measurement channels 50/60 by using the reference channel 50 for real-time scaling so that various environmental effects can be accounted for during operation and analysis. Although the detectors 112/122 may still respond differently to changes in environmental conditions, through calibration, it is possible to scale the output of the measurement detectors 122A-B with the output of the reference detectors 112A-B, thereby compensating for environmental induced spectral changes in the source assembly (40) or environmentally induced responsivity changes of the detectors 112A-B/122A-B in real-time. In addition, the control circuitry 130 can use the reference channel (50) as real-time feedback to control operation of the source assembly (40) and to dynamically improve the signal-to-noise ratio through real-time control of spectral acquisition parameters.

1. Correlating Detected Signals Using Dynamic Referencing

In dynamic scaling, for example, the control circuitry 130 uses the reference channel (50) to dynamically scale the measurement channel (60). To do this scaling, the signal processing circuitry 150 first processes the measurement and reference channels (50/60) by deconvolving their detected spectral signals based on the type of encoding used to encode the signals output by the source assembly (40). Depending on the implementation, for example, the circuitry 150 can deconvolve the signals based on Conventional Raster Scanning (CRS) encoding, Fast Fourier Transform (FFT) encoding, other temporal encoding, Hadamard encoding, other spectral encoding, or the like. Then, the signal processing circuitry 150 temporally syncs the deconvolved measurement and reference signals and scales the amplitude values of the deconvolved measurement signal using the amplitude values of the deconvolved reference signal.

The result of this scaling is a measurement signal (166) that has been corrected in real-time for variations caused by disparate responses, such as but not limited to temperature changes, drift in the source (42) operation, and drift in the detector assembly's electronics. The output 166 of the interface 160 can then send the scaled signal to other components of the measurement device (30; FIG. 2A), such as the source assembly (40), another controller, or other destination.

2. Configuring Source Assembly Using Dynamic Referencing

In addition to correlating detected signals, the control circuitry 130 can use the response from the reference detectors 112A-B as feedback to configure the output of the source assembly (40) so the source assembly (40) can maintain a relatively flat or consistent illumination profile across an entire temperature range that may be experienced downhole. To do this, the control circuitry can use the detected signals from the reference channel (50) as an indication when changes in pulse width modulation, intensity, or the like need to be made for the spectral signals output from the source assembly (40) so that the signals for both the measurement and reference channels (50/60) are improved.

In addition to determining changes directly through dynamic referencing, the control circuitry 130 can also receive data of environmental conditions downhole from one or more external transducers 80, including but not limited to pressure and temperature transducers. The control circuitry 130 can then use these environmental conditions measured downhole in conjunction with the dynamic referencing of the reference channel (50) to compensate the operation of the detector units 110B/120B and the source assembly (40) to account for issues with temperature changes, drift in the source's operation, and drift in the assembly's electronics caused by such environmental conditions. For example, the control circuitry can use the information from the external transducers as input to a scaling function or a lookup table employed to scale the processed measurement signal. This scaling can thereby account for spectral changes that would be caused by the environmental conditions detected by the transducers.

To configure the output of the source assembly (40), the control circuitry 130 can trigger the source assembly (40), which may have its own controller, to change its operating parameters to account for the environmental changes determined through the dynamic referencing and/or external transducers 80. Alternatively, the control circuitry 130 can directly control the source assembly (40) by configuring its operating parameters and sending control signals to the assembly (40) for operation.

In one brief example of such direct control, the control circuitry 130 can initially configure how the sources (42) in the source assembly (40) are to be operated and can send control signals to the source assembly (40) to implement the configured operation. For example, the control circuitry 130 may configure the amplitude at which to operate the sources (42), thereby altering or increasing the overall optical intensity of the signals. Alternatively, the control circuitry 130 may configure one or more modulated pulse trains used for controlling the illumination of the sources (42) and can send temporal characteristics (start time, pulse frequency, duty cycle, or pulse shape) of the pulse trains to the source assembly (40) to implement when operating the sources (42).

As the source assembly (40) then generates spectral signals as configured, the control circuitry 130 detects the spectral signals generated by the source assembly (40) using the reference detector unit 110B. By comparing the detected signal to how the output is configured for the source, the signal processing circuitry 150 can determine what discrepancies exist between how the source assembly (40) is being operated and how the spectral signals are being detected, and the control circuitry 130 can correlate any discrepancies to spectral changes caused by the environmental conditions. Based on this analysis, the control circuitry 130 can then make modifications to how it controls the source assembly (40), thereby controlling the illumination and resulting amplitude of the source assembly (40) to maintain a relatively flat or consistent illumination profile despite large environmental changes.

G. Detection/Signal Processing Modes

In addition to dynamic referencing, the detector assembly 100 can be operated in one or more detection/signal processing modes that can give operators control over scan speed, signal-to-noise ratio, and process monitoring methodology. In general, these processing modes for the detector assembly 100 can be implemented as software or the like in the control circuitry 130. Depending on the implementation, the assembly 100's hardware components (FPGA, ADC, multiplexers, etc.) can be specifically configured to operate utilizing one of the particular modes or can be configured to operate under several of these different modes. In this way, operating the detector assembly 100 in one of the desired modes may simply require programming changes to the control circuitry 130, which can occur during installation or even during downhole use via the interface 160. Depending on the implementation, the detection and signal processing in each of these modes may be performed separately on each channel 50/60 using the spectral signals from the separate detection units 110/120. Likewise, the processing of each channel 50/60 may be performed separately on the detected bands from each detector in the multi-band arrangements.

1. Conventional Raster-Scanning Mode

In a first detection/signal processing mode, the detector assembly 100 can be operated using raster-scanning. In this mode, the control circuitry 130 configures the source assembly (40) to illuminate each source (42) sequentially one at a time, and the control circuitry 130 can correlate both the reference and measurement channel (50/60) measurements for each source (42) in a serial fashion, thereby acquiring a full spectral scan over time. This mode does not require source modulation.

Alternatively, the control circuitry 130 configures the source assembly (40) to illuminate each source (42) sequentially one at a time with each source (42) being oscillated at a fixed frequency common to all the sources (42) to improve the signal-to-noise ratio. Then, the control circuitry 130 can perform raster scanning with lock-in detection of the reference and measurement channels (50/60) detected by the detector units 110B/120B. The lock-in detection can be implemented by digital filtering, absolute value determination, averaging and any other techniques known to those skilled the art of signal analysis.

Either way, the reference and measurement channels (50/60) are immediately correlated, and the modulated signal received at the reference and measurement detector units 110B/120B can then be used during data processing. Operation of the detector assembly 100 in this mode can allow for easy noise level versus integration time tradeoffs. Ultimately, the control circuitry 130 needed to operate in this mode may require less complexity which may be beneficial for downhole use.

2. Channel Select Raster Scanning

A second detection/signal processing mode is a modified form of raster scanning. In this mode, the control circuitry 130 configures the source assembly (40) to illuminate a reduced number of the available spectral sources (42) (e.g., LEDs) in the source assembly (40). When a change is detected in the spectral bands for these select sources (42), the control circuitry 130 configures the source assembly (40) to operate under full raster-scanning mode as discussed above so that a complete spectral scan can be run for further discrimination of the sample fluid being measured. This modified raster-scanning mode allows the detector assembly 100 to run relatively fast and with more flexibility in meeting the requirements of an intended application.

3. Fast-Fourier-Transform (FFT) Mode

In a third detection/signal processing mode, the control circuitry 130 configures the source assembly (40) to illuminate all the sources (42) (e.g., LEDs) of the source assembly (40) simultaneously so their spectral signals can all be processed simultaneously. This FFT mode offers synchronous full spectral scanning of the fluid properties and can also lead to an improved signal-to-noise (S/N) ratio under most environmental conditions. To operate under this FFT mode with the source assembly (40) having multiple sources (42) such as LEDs, the control circuitry 130 may need to simultaneously process in excess of 256 channels of data for the dual band arrangement of the detector assembly 100 as in FIG. 10.

In this mode, the control circuitry 130 configures the sources (42) to illuminate the sample in the sample assembly (70; FIG. 2A) simultaneously with all sources (42), and the detector assembly 100 uses FFT operations for single shot data acquisition across the entire measurement range. To do this, the control circuitry 130 configures each source (42) to modulate at an independent frequency, and the control circuitry 130 de-convolutes the signals detected from the measurement and reference detector units 110B/120B using FFT analysis to provide intensity information for later data processing. In this mode, a sample time is used to set the frequency resolution. In addition, the amplitude accuracy of the measurement is set by an Analog-to-Digital converter's bit resolution, the sample duration and frequency, the number of scans averaged, and the signal-to-noise ratio of the detector units 110/120.

4. Fixed Frequency Analysis (FFA) Mode

Figure 13:
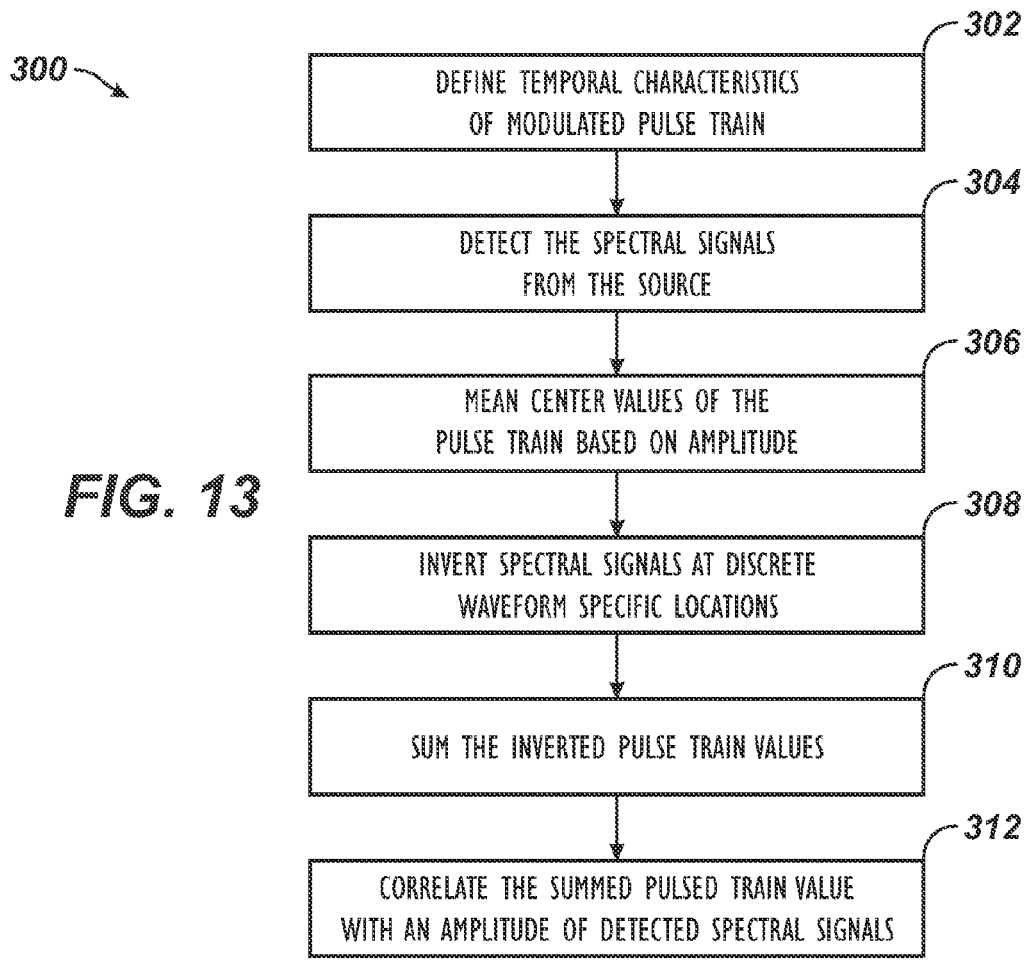
FIG. 13 shows a process for performing a fixed frequency analysis mode of operation.

In a fourth detection/signal processing mode, which is similar in terms of simultaneous excitation to the FFT mode, the detector assembly 100 uses a fixed frequency analysis (FFA) mode in which a set of fixed frequencies that have predefined properties are used for illuminating the sources (42) (e.g., LEDs). Referring concurrently to the detector assembly 100 in FIG. 10 and a process 300 in FIG. 13, the control circuitry 130 in this FFA mode configures the sources (42) to pulse simultaneously using fixed frequency increments, and the control circuitry 130 configures the waveforms to pulse the sources (42) based on an integer number of cycles. To do this, the control circuitry 130 can define the temporal characteristics (start time, frequency, duty cycle, and phase delay) of a modulated pulse train used for operating the sources (42) based on the fixed frequency increments and predefined properties (Block 302). Then the control circuitry 130 sends the modulated pulse train to the source assembly (40) to implement.

Figure 14A:
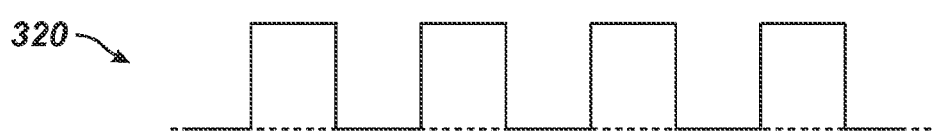
FIGS. 14A-14C show examples of signals during processing under the mode of FIG. 11.

As the source assembly (40) generates spectral signals based on the modulated pulse train, the control circuitry 130 performs spectral de-convolution of the detected signals using a predefined numerical method for signal analysis that is based on the known temporal characteristics of the configured waveform. In particular, the detector assembly 100 detects the amplitude (intensity) of the detected signals (320; FIG. 14A) from the sources (42) having the known modulated pulse train (Block 304).

Figure 14B:
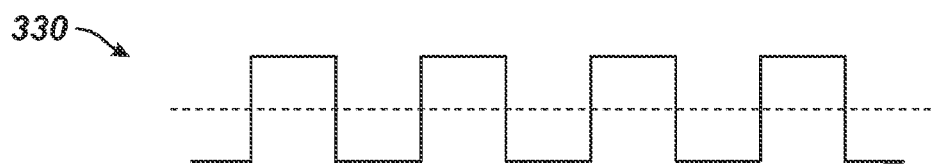
Figure 14C:

The control circuitry 130 mean centers the amplitude of the detected signals to create a mean centered signal (230; FIG. 14B) (Block 306) and then inverts values in the mean centered signal at discrete waveform specific locations (i.e., times) of the known modulated pulse train to create an inverted signal (240; FIG. 14C) (Block 308). At this point, the control circuitry 130 sums the mean centered, inverted pulse train values to form a summed pulse train value (Block 310). Then, the control circuitry 130 correlates this summed pulsed train value with the amplitude of the detected spectral signals so that subsequent analysis can be performed to determine characteristics of the sample fluid (Block 312).

In this technique, the modulated pulse train requires a signal phase shift that is known or negligibly small relative to the modulation frequency used. In addition, the minimum sample period used in the analysis is preferably greater than $1/\Delta f$, where $\Delta f$ is the frequency increment above the fundamental frequency ($f_0$) used to illuminate the individual sources (42). Finally, no odd multiples of the frequency f (i.e. 1 kHz and 3 kHz) are used to pulse the sources (42).

This FFA mode produces similar results as the FFT mode discussed above. However, the FFA mode may be preferred because implementing this FFA mode in hardware is simpler compared to the hardware requirements for performing the analysis in the FFT mode discussed previously. In particular, the FFA mode reduces the computational load on the downhole control circuitry 130, reducing overall component size and power requirements. Compared to the FFT mode which requires $2^n$ channels, the data processing in the FFA mode is faster because it only uses as many channels as needed. Any signal lag between acquisition and visualization can, therefore, be significantly reduced. In addition, the rate of data acquisition can be easily changed in conjunction with signal averaging for signal-to-noise ratio improvement.

5. Asynchronous Hadamard Transform Encoding

In yet another operational mode, the control circuitry 130 operates the sources (42) using asynchronous Hadamard Transform encoding. In this mode, the control circuitry 130 configures the source assembly (40) to illuminate a unique sequence of a subset of sources (42) (e.g., LEDs) in a cyclic fashion with only one subset of sources (42) in operation at a given point in time. While operating in this mode, each source (42) may also be modulated at independent frequencies. In turn, the control circuitry 130 de-convolutes the signals detected from the measurement and reference detector units 110B/120B using Hadamard analysis to provide intensity information for later data processing.

The foregoing description of preferred and other embodiments is not intended to limit or restrict the scope or applicability of the inventive concepts conceived of by the Applicants. Although several detection/signal processing modes for the detection assembly 100 have been discussed above, for example, it will be appreciated that the assembly 100 can be operated based on other modes of operation known to those skilled in the art.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A detector assembly for downhole spectroscopy used in conjunction with one or more light emitters of a source assembly, the detector assembly comprising:
a reference unit having at least one reference detector and detecting first spectral signals across a spectral range of wavelengths from a reference channel of the one or more light emitters;
a measurement unit having at least one measurement detector and detecting second spectral signals across the spectral range of wavelengths from a measurement channel of the one or more light emitters after interaction with a fluid sample;
conversion circuitry communicatively coupled to the reference and measurement units and converting the first and second spectral signals into reference signals and measurement signals; and
control circuitry communicatively coupled to the conversion circuitry and to the one or more light emitters of the spectral signals, the control circuitry processing the reference and measurements signals and configuring output of the spectral signals from the one or more light emitters based at least on the processed reference signals,
wherein to configure the output, the control circuitry at least controls the one or more light emitters to configure light emitter intensity.

2. The assembly of claim 1, wherein the reference and measurement detectors are selected from the group consisting of a single-element photodiode, a multi-element photodiode, an avalanche photodiode, a photomultiplier tube, a microchannel plate, a bolometer, and a thermopile.

3. The assembly of claim 1, wherein the reference unit comprises—
a plurality of the reference detectors, and
a first router partitioning the reference channel into a plurality of first beams and routing each of the first beams to one or more of the reference detectors.

4. The assembly of claim 3, wherein the first router comprises at least one optical element disposed in an optical path of the reference channel.

5. The assembly of claim 4, wherein the at least one optical element is selected from the group consisting of a wavelength selection elements, a high-pass filter, a low-pass filter, and a dichroic element.

6. The assembly of claim 4, wherein each of the first beams comprises a unique spectral band different from the other first beams.

7. The assembly of claim 4, wherein the at least one optical element comprises an adaptive optical element oscillatable between at least two orientations in the optical path of the reference channel, each of the at least two orientations corresponding to one of the first beams.

8. The assembly of claim 3, wherein the measurement unit comprises—
a plurality of the measurement detectors, and
a second router partitioning the measurement channel into a plurality of second beams and routing each of the second beams to one or more of the measurements detectors.

9. The assembly of claim 8, wherein the measurement detectors and the second beams correspond in arrangement to the reference detectors and the first beams.

10. The assembly of claim 1, wherein to process the signals and configure the output, the control circuitry dynamically scales the measurement signal using the reference signal.

11. The assembly of claim 1, wherein to process the signals and configure the output, the control circuitry deconvolves the measurement and reference signals based on a type of encoding used to encode the spectral signals output by the one or more light emitters.

12. The assembly of claim 11, wherein the control circuitry deconvolves the signals based on Raster Scanning encoding, Fast Fourier Transform encoding, other temporal encoding, Hadamard encoding, or other spectral encoding.

13. The assembly of claim 1, wherein to process the signals and configure the output, the control circuitry temporally syncs the output of the one or more light emitters with at least the first spectral signals detected by the at least one reference detector to determine temporal characteristics of the one or more light emitters.

14. The assembly of claim 1, wherein to process the signals and configure the output, the control circuitry scales the measurement signal with the reference signal to compensate for a fluctuation in the one or more light emitters or a change in an environmental condition.

15. The assembly of claim 1, wherein to process the signals and configure the output, the control circuitry scales the output of the one or more light emitters to account for spectral changes caused by environmental conditions.

16. The assembly of claim 1, wherein the control circuitry receives data of one or more environmental conditions from one or more external transducers, and wherein the control circuitry scales the measurement signal, the reference signals, or both the measurement and reference signals based on spectral changes indicated by the one or more environmental conditions.

17. The assembly of claim 1, wherein to process the signals and configure the output, the control circuitry configures a modulated pulse train for controlling illumination of the one or more light emitters.

18. The assembly of claim 17, wherein to configure the modulated pulse train, the control circuitry defines at least one temporal characteristic of the modulated pulse train, wherein the at least one temporal characteristic includes start time, pulse frequency, duty cycle, or pulse shape.

19. The assembly of claim 17, wherein to process the signals and configure the output, the control circuitry is configured to:
    mean center values of the detected modulated pulse train;
    invert the mean centered values of the detected pulse trains at discrete temporal locations;
    sum the inverted pulse train values; and
    correlate the summed pulsed train value with an amplitude of the spectral signals.

20. A downhole fluid analysis tool, comprising:
    a tool housing deployable downhole and having a flow passage for a fluid sample; and
    a fluid analysis device disposed in the tool housing relative to the flow passage, the fluid analysis device at least including:
        one or more light emitters outputting spectral signals across a spectral range of wavelengths and partitioning the spectral signals into a reference channel and a measurement channel,
        a reference unit having at least one reference detector and detecting first spectral signals from the reference channel,
        a measurement unit having at least one measurement detector and detecting second spectral signals from the measurement channel,
        conversion circuitry communicatively coupled to the reference and measurement units and converting the first and second spectral signals into reference signals and measurement signals, and
        control circuitry communicatively coupled to the conversion circuitry and to the one or more light emitters of the spectral signals, the control circuitry processing the reference and measurements signals and configuring output of the spectral signals from the one or more light emitters based at least on the processed reference signals,
        wherein to configure to output, the control circuitry at least controls the one or more light emitters to configure light emitter intensity.

21. The method of claim 20, wherein processing the signals and configuring the output comprises dynamically scaling the measurement signal with the reference signal.

22. The method of claim 21, wherein dynamically scaling the measurement signal with the reference signal comprises compensating for a fluctuation in the one or more light emitters or a change in an environmental condition.

23. A downhole spectroscopy method, comprising:
    detecting first spectral signals across a spectral range of wavelengths from a reference channel output by one or more light emitters using at least one reference detector;
    detecting second spectral signals across the spectral range of wavelengths form a measurement channel output by the one or more light emitters after interaction with a fluid sample using at least one measurement detector;
    digitizing the first and second spectral signals into reference and measurement signals;
    processing the reference and measurement signals; and
    configuring output of the spectral signals from the one or more light emitters based at least on the processed reference signals,
    wherein configuring the output at least includes controlling the one or more light emitters to configure light emitter intensity.

24. The method of claim 23, wherein the detectors are selected from the group consisting of single-element photodiodes, multi-element photodiodes, avalanche photodiodes, photomultiplier tubes, micro-channel plates, bolometers, and thermopiles.

25. The method of claim 23, wherein the at least one reference detector comprises a plurality of reference detectors, and wherein the method comprises partitioning the reference channel into a plurality of first beams and routing each of the first beams to one of the reference detectors.

26. The method of claim 25, wherein partitioning the reference channel comprises disposing at least one optical element in an optical path of the reference channel and partitioning the reference channel into at least two beams with the at least one optical element.

27. The method of claim 26, wherein the at least one optical element is selected from a high-pass filter, a low-pass filter, and a dichroic element.

28. The method of claim 26, wherein each of the first beams comprises a unique spectral band different from the other first beams.

29. The method of claim 26, wherein the at least one optical element comprises an adaptive optical element oscillatable between at least two orientations in the optical path of the reference channel, each of the at least two orientations corresponding to one of the first beams.

30. The method of claim 25, wherein the at least one measurement detector comprises a plurality of measurement detectors, and wherein the method comprises partitioning the measurement channel into a plurality of second beams and routing each of the second beams to one of the measurements detectors.

31. The method of claim 30, wherein the measurement detectors and the second beams correspond in arrangement to the reference detectors and the first beams.

32. The method of claim 23, wherein processing the signals and configuring the output comprises deconvolving the signals based on a type of encoding used to encode the spectral signals output by the one or more light emitters.

33. The method of claim 32, wherein the encoding used includes Raster Scanning encoding, Fast Fourier Transform encoding, other temporal encoding, Hadamard encoding, or other spectral encoding.

34. The method of claim 23, wherein processing the signals and configuring the output comprises temporally syncing the spectral signals output by the one or more light emitters with the spectral signals at least detected by the at least one reference detector.

35. The method of claim 23, wherein processing the signals and configuring the output comprises accounting for spectral changes caused by environmental conditions by scaling the spectral signals output by the one or more light emitters.

36. The method of claim 23, wherein processing the signals and configuring the output comprises:

receiving data of one or more environmental conditions from one or more external transducers, and scaling the measurement signal, the reference signals, or both the measurement and reference signals based on spectral changes indicated by the one or more environmental conditions.

37. The method of claim 23, wherein processing the signals and configuring the output comprises configuring a modulated pulse train for illuminating the one or more light emitters.

38. The method of claim 37, wherein configuring the modulated pulse train comprises defining at least one temporal characteristic of the pulse train, wherein the at least one temporal characteristic includes start time, pulse frequency, duty cycle, or pulse shape.

39. The method of claim 37, wherein processing the signals and configuring the output comprises:
mean centering values of the detected pulse train;
inverting the mean centered values of the detected pulse trains at discrete temporal locations;
summing the inverted pulse train values; and
correlating the summed pulsed train value with an amplitude of the spectral signal from the one or more light emitters.

40. A downhole fluid analysis method, comprising:
deploying a tool downhole, the tool having a flow passage for a fluid sample; and analyzing the fluid sample by—
operating one or more light emitters to generate spectral signals across a spectral range of wavelengths in a reference channel and a measurement channel,
detecting the spectral signals of the reference channel using at least one reference detector,
detecting the spectral signals from the measurement channel after interaction with the fluid sample using at least one measurement detector,
digitizing the spectral signals sensed by the at least one reference detector into reference signals;
digitizing the spectral signals sensed by the at least one measurement detectors into measurement signals,
processing the reference and measurement signals, and
controlling output of the spectral signals from the one or more light emitters based at least on the processed reference signals,
wherein controlling the output at least includes controlling the one or more light emitters to configure light emitter intensity.

* * * * *